(12) United States Patent
Krafft

(10) Patent No.: US 8,344,185 B2
(45) Date of Patent: Jan. 1, 2013

(54) METHOD FOR MAKING A CHLORHYDRINE BY REACTION BETWEEN A POLYHYDROXYLATED ALIPHATIC HYDROCARBON AND A CHLORINATING AGENT

(75) Inventor: Philippe Krafft, Rhode Saint Genese (BE)

(73) Assignee: Solvay (Société Anonyme, Brussels (BE)

( * ) Notice: Subject to any disclaimer, the term of this patent is extended or adjusted under 35 U.S.C. 154(b) by 1175 days.

(21) Appl. No.: 11/914,868

(22) PCT Filed: May 19, 2006

(86) PCT No.: PCT/EP2006/062448
§ 371 (c)(1),
(2), (4) Date: Nov. 19, 2007

(87) PCT Pub. No.: WO2006/106153
PCT Pub. Date: Oct. 12, 2006

(65) Prior Publication Data
US 2008/0200642 A1  Aug. 21, 2008

Related U.S. Application Data

(60) Provisional application No. 60/734,635, filed on Nov. 8, 2005, provisional application No. 60/734,657, filed on Nov. 8, 2005, provisional application No. 60/734,636, filed on Nov. 8, 2005, provisional application No. 60/734,627, filed on Nov. 8, 2005, provisional application No. 60/734,634, filed on Nov. 8, 2005, provisional application No. 60/734,658, filed on Nov. 8, 2005, provisional application No. 60/734,637, filed on Nov. 8, 2005, provisional application No. 60/734,659, filed on Nov. 8, 2005.

(30) Foreign Application Priority Data

May 20, 2005  (EP) ..................................... 05104321
May 20, 2005  (FR) ..................................... 05 05120

(51) Int. Cl.
C07C 29/62  (2006.01)
(52) U.S. Cl. ....................................... 568/841; 568/844
(58) Field of Classification Search .................. 568/844, 568/841
See application file for complete search history.

(56) References Cited

U.S. PATENT DOCUMENTS

| | | | |
|---|---|---|---|
| 280,893 A | 7/1883 | Baujard |
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Hermann |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak, et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |

(Continued)

FOREIGN PATENT DOCUMENTS

BE  422877  8/1937

(Continued)

OTHER PUBLICATIONS

Sigma Chemical Catalog {1994; Hydrochloric Acid having product No. [7647-01-0]}.*

(Continued)

*Primary Examiner* — Kamal Saeed
(74) *Attorney, Agent, or Firm* — Oblon, Spivak, McClelland, Maier & Neustadt, L.L.P.

(57) ABSTRACT

Process for preparing a chlorohydrin from a polyhydroxylated aliphatic hydrocarbon, from an ester of a polyhydroxylated aliphatic hydrocarbon or from a mixture thereof, and from a chlorinating agent, the chlorinating agent comprising at least one of the following compounds: nitrogen, oxygen, hydrogen, chlorine, an organic hydrocarbon compound, an organic halogen compound, an organic oxygen compound and a metal.

25 Claims, 1 Drawing Sheet

U.S. PATENT DOCUMENTS

| | | | |
|---|---|---|---|
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,595,469 A | 6/1986 | Foller |
| 4,609,751 A | 9/1986 | Hajjar |
| 4,634,784 A | 1/1987 | Nagato et al. |
| 4,655,879 A | 4/1987 | Brockmann et al. |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer, Jr. et al. |
| 5,567,359 A | 10/1996 | Cassidy et al. |
| 5,578,740 A | 11/1996 | Au et al. |
| 5,710,350 A | 1/1998 | Jeromin et al. |
| 5,731,476 A | 3/1998 | Shawl et al. |
| 5,744,655 A | 4/1998 | Thomas et al. |
| 5,779,915 A | 7/1998 | Becker et al. |
| 5,908,946 A | 6/1999 | Stern et al. |
| 5,993,974 A | 11/1999 | Fukushima et al. |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,719,957 B2 | 4/2004 | Brady, Jr. et al. |
| 6,740,633 B2 | 5/2004 | Norenberg et al. |
| 7,126,032 B1 | 10/2006 | Aiken |
| 7,128,890 B2 | 10/2006 | Ollivier |
| 7,584,629 B2 | 9/2009 | Sohn et al. |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel, Jr. |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0293707 A1 | 12/2007 | Wolfert et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0281132 A1 | 11/2008 | Krafft et al. |
| 2009/0022653 A1 | 1/2009 | Strebelle et al. |
| 2009/0173636 A1 | 7/2009 | Ooms et al. |
| 2009/0198041 A1 | 8/2009 | Krafft et al. |
| 2010/0029959 A1 | 2/2010 | Fan et al. |

FOREIGN PATENT DOCUMENTS

| | | |
|---|---|---|
| CA | 1119320 | 8/2003 |
| CN | 1296003 A | 5/2001 |
| CN | 101041421 | 9/2007 |
| DE | 58396 | 8/1891 |
| DE | 180 668 | 1/1906 |
| DE | 197 308 | 11/1906 |
| DE | 238 341 | 3/1908 |
| DE | 869 193 | 3/1953 |
| DE | 1 041 488 | 10/1958 |
| DE | 1 075 103 | 2/1960 |
| DE | 1 226 554 | 10/1966 |
| DE | 2 241 393 | 2/1974 |
| DE | 25 21 813 | 12/1975 |
| DE | 30 03 819 | 8/1981 |
| DE | 216 471 | 6/1983 |
| DE | 32 43 617 | 5/1984 |
| DE | 37 21 003 | 6/1987 |
| DE | 43 02 306 | 8/1994 |
| DE | 43 35 311 | 4/1995 |
| DE | 102 03 914 | 1/2002 |
| DE | 102 54 709 | 6/2004 |
| DE | 238341 | 3/2008 |
| DE | 197 309 | 4/2008 |
| EP | 0 296 341 | 12/1988 |
| EP | 0 347 618 | 12/1989 |
| EP | 0 421 379 | 4/1991 |
| EP | 0 452 265 | 10/1991 |
| EP | 0 518 765 | 12/1992 |
| EP | 0 522 382 | 1/1993 |
| EP | 0 535 949 | 4/1993 |
| EP | 0 563 720 | 10/1993 |
| EP | 0 568 389 | 11/1993 |
| EP | 0 582 201 | 2/1994 |
| EP | 0 618 170 | 10/1994 |
| EP | 0 916 624 | 5/1999 |
| EP | 0 919 551 | 6/1999 |
| EP | 0 774 450 | 2/2000 |
| EP | 1 059 278 | 12/2000 |
| EP | 1 106 237 | 6/2001 |
| EP | 1 153 887 | 11/2001 |
| EP | 1 163 946 | 12/2001 |
| EP | 1 231 189 | 8/2002 |
| EP | 1 298 154 | 4/2003 |
| EP | 0 561 441 | 9/2003 |
| EP | 1 411 027 | 4/2004 |
| EP | 1 752 435 | 2/2007 |
| EP | 1 752 436 | 2/2007 |
| EP | 1 760 060 | 3/2007 |
| EP | 1 762 556 | 3/2007 |
| EP | 1 770 081 | 4/2007 |
| EP | 1 772 446 | 4/2007 |
| EP | 1 775 278 | 4/2007 |
| EP | 2 085 364 | 8/2009 |
| FR | 1 306 231 | 10/1961 |
| FR | 1 417 388 | 10/1964 |
| FR | 1 476 073 | 4/1966 |
| FR | 1 577 792 | 8/1968 |
| FR | 2 180 138 | 5/1973 |
| FR | 2 217 372 | 2/1974 |
| FR | 2 565 229 | 12/1985 |
| FR | 2 752 242 | 2/1998 |
| FR | 2 862 644 | 5/2005 |
| FR | 2 868 419 | 10/2005 |
| FR | 2 869 612 | 11/2005 |
| FR | 2 869 613 | 11/2005 |
| FR | 2 872 504 | 1/2006 |
| FR | 2 881 732 | 8/2006 |
| FR | 2 885 903 | 11/2006 |
| FR | 2 912 743 | 8/2008 |
| FR | 2 913 683 | 9/2008 |
| FR | 2 917 411 | 12/2008 |
| FR | 2 918 058 | 1/2009 |
| FR | 2 925 045 | 6/2009 |
| FR | 2 929 611 | 10/2009 |
| FR | 2 935 699 | 3/2010 |
| FR | 2 935 968 | 3/2010 |
| GB | 14 767 | 0/1914 |
| GB | 404 938 | 7/1932 |

| | | |
|---|---|---|
| GB | 406345 | 8/1932 |
| GB | 467 481 | 9/1935 |
| GB | 541357 | 11/1941 |
| GB | 679 536 | 9/1952 |
| GB | 736641 | 7/1953 |
| GB | 799 567 | 8/1958 |
| GB | 1046521 | 1/1964 |
| GB | 1083594 | 11/1964 |
| GB | 984446 | 2/1965 |
| GB | 984 633 | 3/1965 |
| GB | 1 387 668 | 3/1972 |
| GB | 1286893 | 8/1972 |
| GB | 1 493 538 | 4/1975 |
| GB | 1 414 976 | 11/1975 |
| GB | 2 173 496 | 10/1986 |
| GB | 702143 | 10/1990 |
| GB | 2 336 584 | 10/1999 |
| HU | 2002-003023 | 3/2004 |
| JP | 39-27230 | 11/1928 |
| JP | 50-062909 | 5/1975 |
| JP | 55-041858 | 3/1980 |
| JP | 56-29572 | 3/1981 |
| JP | 56-99432 | 8/1981 |
| JP | 61-112066 | 5/1986 |
| JP | 61-236749 | 10/1986 |
| JP | 62-242638 | 10/1987 |
| JP | 63-195288 | 8/1988 |
| JP | 2-137704 | 5/1990 |
| JP | 03-014527 | 1/1991 |
| JP | 3-223267 | 10/1991 |
| JP | 03-223267 | 10/1991 |
| JP | 04-089440 | 3/1992 |
| JP | 04-217637 | 8/1992 |
| JP | 6-25196 | 4/1994 |
| JP | 6-184024 | 7/1994 |
| JP | 06-321852 | 11/1994 |
| JP | 8-59593 | 3/1996 |
| JP | 09-299953 | 11/1997 |
| JP | 10-139700 | 5/1998 |
| JP | 10-218810 | 8/1998 |
| JP | 2000-344692 | 12/2000 |
| JP | 2001-037469 | 2/2001 |
| JP | 2001-213827 | 8/2001 |
| JP | 2001-261308 | 9/2001 |
| JP | 2001-1261581 | 9/2001 |
| JP | 2002-02033 | 1/2002 |
| JP | 2002-038195 | 2/2002 |
| JP | 2002-265986 | 9/2002 |
| JP | 2002-363153 | 12/2002 |
| JP | 2003-81891 | 3/2003 |
| JP | 2003-89680 | 3/2003 |
| JP | 2005-007841 | 1/2005 |
| JP | 2005-097177 | 4/2005 |
| JP | 76021635 | 4/2005 |
| JP | 2007-008898 | 1/2007 |
| JP | 2009-263338 | 11/2009 |
| KR | 900006513 | 11/1987 |
| KR | 2003-29740 | 5/2003 |
| KR | 10-0514819 | 11/2004 |
| SU | 123153 | 1/1959 |
| SU | 1125226 | 11/1984 |
| SU | 1159716 | 6/1985 |
| SU | 1685969 | 10/1991 |
| WO | WO 95/14639 | 6/1995 |
| WO | WO 96/07617 | 3/1996 |
| WO | WO 96/15980 | 5/1996 |
| WO | WO 97/48667 | 12/1997 |
| WO | WO 98/37024 | 8/1998 |
| WO | WO 99/14208 | 3/1999 |
| WO | WO 99/32397 | 7/1999 |
| WO | WO 00/24674 | 5/2000 |
| WO | WO 01/41919 | 6/2001 |
| WO | WO 01/86220 | 11/2001 |
| WO | WO 02/26672 | 4/2002 |
| WO | WO 03/064357 | 8/2003 |
| WO | WO 2004/056758 | 7/2004 |
| WO | WO 2005/021476 | 3/2005 |
| WO | WO 2005/054167 | 6/2005 |
| WO | WO 2005/097722 | 10/2005 |
| WO | WO 2005/115954 | 12/2005 |
| WO | WO 2005/116004 | 12/2005 |
| WO | WO 2006/020234 | 2/2006 |
| WO | WO 2006/100311 | 9/2006 |
| WO | WO 2006/100312 | 9/2006 |
| WO | WO 2006/100313 | 9/2006 |
| WO | WO 2006/100314 | 9/2006 |
| WO | WO 2006/100315 | 9/2006 |
| WO | WO 2006/100316 | 9/2006 |
| WO | WO 2006/100317 | 9/2006 |
| WO | WO 2006/100318 | 9/2006 |
| WO | WO 2006/100319 | 9/2006 |
| WO | WO 2006/100320 | 9/2006 |
| WO | WO 2006/106153 | 10/2006 |
| WO | WO 2006/106154 | 10/2006 |
| WO | WO 2006/106155 | 10/2006 |
| WO | WO 2007/005405 | 5/2007 |
| WO | WO 2007/054505 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/026212 | 2/2009 |
| WO | WO 2009/043796 | 4/2009 |
| WO | WO 2009/077528 | 6/2009 |
| WO | WO 2009/095429 | 8/2009 |
| WO | WO 2009/121853 | 10/2009 |
| WO | WO 2010/029039 | 3/2010 |
| WO | WO 2010/029153 | 3/2010 |
| WO | WO 2010/066660 | 6/2010 |

OTHER PUBLICATIONS

Perry's Chemical Engineers Handbook 7$^{th}$ Ed. 11$^{th}$ Section, 1997.
Perry's Chemical Engineers Handbook 7$^{th}$ Ed. 13$^{th}$ Section, 1997.
Perry's Chemical Engineers Handbook 7$^{th}$ Ed. 15$^{th}$ Section, 1997.
Ullmann Encyclopedia Industr. Chem. 5$^{th}$ Ed., vol. A23, 1993 pp. 635-636.
Ullmann Encyclopedia Industr. Chem. 5$^{th}$ Ed., vol. A13, 1989 pp. 289.
Ullmann Encyclopedia Industr. Chem. 5$^{th}$ Ed., vol. A11, 1988 pp. 354-360.
Production and Prospect of the World Natural Glycerol by Zhu Shiyong, Cereals and Oils, vol. 1, 1997, pp. 33-38 (No English Translation).
Vinnolit; Vinnolit receives EU grant for water recycling project; Press Release, 2008: http://www.vinnolit.de/vinnolit.nsf/id/EN__Vinnolit_receives_EU_grant_for_water_recycling_project_.
N.W. Ziels, Journal of American Oil Chemists' Society, Nov. 1956, vol. 33, pp. 556-565.
Perry's Chemical Engineers Handbook, Sixth Edition, McGraw Hill Inc., (1984) Section 18.
Vol. B3: Unit Operations II of Ullmann's Encyclopedia of Industrial Chemistry, Fifth Completely Revised Edition, Published by VCH, 1988.
Armando Novelli, "The Preparation of Moni- and Dichlorohydrins of Glycerol," Anal. Farm. Bioquim. vol. 1, 1930, pp. 8-19 (with English Abstract).
Kirk-Othmer Encyclopedia of Chemical Technology, Third Edition, vol. 4, Blood, Coagulants and Anticoagulants to Cardiovascular Agents.
Kirk Othmer Encyclopedia of Chemical Technology, Third Edition, vol. 12, 1980, pp. 1002-1005.
Chemical Engineering Handbook, the 6$^{th}$ Edition, Edited by the Chemical Engineers, published by Maruzen Co., Ltd., 1999, pp. 1296-1306 w/English translation of p. 1296, Table 28.4, p. 1298, left col., lines 4-13 and p. 1305, Table 28.10.
Product Brouchure of De Dietrich Company, Apr. 1996, pp. 3, 8 and 9 w/English translation of p. 8, left col., lines 1-4, p. 9.

The Journal of the American Chemical Society, vol. XLV, Jul.-Dec. 1923, pp. 2771-2772.
Berichte Der Deutschen Chemischen Gesellschaft, 1891, vol. 24, pp. 508-510.
Ma Zengxin, Gan Yicui, Recovery of Polyglycerol from Residues of Synthetic Glycerol—Riyong Huaxue Gongye, 1997, 4, 21023 (Abstract Only).
Ullmann's Encyclopedia of Industrial Chemistry, 2005, Wiley-VCH GmbH & Co., KgaA, Weinhem, pp. 8-15 and 401-477, Published online Mar. 15, 2001.
RD 436093, Aug. 10, 2000, Research Disclosure.
Catalogue of Nittetu Chemical Engineering Ltd. (Published in Mar. 1994).
12093 Chemicals, Chemical Daily Co., Ltd. (Published on Jan. 22, 1993) with attached English translation of relevant excerpts.
Chemicals Guide, Chemical Daily Co., Ltd. (Published on Jun. 15, 1990) with attached English translation of relevant excerpts.
Robert T. Morrison & Robert N. Boyd, Organic Chemistry, vol. II, pp. 666 to 667 and 712 to 714 (Japanese translation), published on Jul. 10, 1970, Tokyo Kagaku Dozin Co., Ltd. (and copies of similar passages but retrieved from the English $5^{th}$ Edition of the Book, 1987.
Jeffrey Lutje Spelberg, et al., A Tandem Enzyme Reaction to Produce Optically Active Halohydrins, Epoxides and Diols, Tetrahedron: Asymmetry, Elsevier Science Publishers, vol. 10, No. 15, pp. 2863-2870.
Oleoline, com, Glycerine Market report, Sep. 10, 2003, No. 62.
Notification Under Act. No. 100/2001, Coll. As Amended by Act No. 93/2004, Coll. To the extent of Annex No. 4, (SPOLEK) Nov. 30, 2004.
Documentation Under Act No. 100/2001 Coll. As amended by Act No. 93/2004 Coll in the scope of appendix No. 4 (SPOLEK) Jan. 11, 2005.
K. Weissermel and H J. Arpe in Industrial Organic Chemistry, Third, Completely Revised Edition, VCH, 1997, pp. 149,275.
Industrial Bioproducts: "Today and Tomorrow," Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & sons, Inc.
Ullmann's Encyclopedia of Industrial Chemistry, Fifth, Completely Revised Edition, 1985, vol. A13, pp. 292-293.
The Merck Index, Eleventh Edition, 1989, pp. 759-760.
Ullmann's Encyclopedia of Industrial Chemistry, Fifth Completely Revised Edition, vol. A1, pp. 427-429.
Ullmann's Encyclopedia of Industrial Chemistry, Fifth Completely REvised Edition, vol. A6, pp. 240-252.
Hancock, E.G., Propylene and its Industrial Derivatives, 1973, pp. 298-332.
K. Weissermel and H. J. Arpe in Industrial Organic Chemistry, Third, Completely Revised Edition, VCH, 1997, pp. 149-163.
K. Weissermel and H. J. Arpe in Industrial Organic Chemistry, Third, Completely Revised Edition, VCH, 1997, pp. 275-276.
Ullmann's Encyclopedia of Industrial Chemistry, Fifth Completely Revised Edition, vol. A9, pp. 539-540.
Perry's Chemical Engineers Handbook, Sixth Edition, Robert H. Perry, Don Green, 1984, Section 21-44 to 21-68.
Iwanami Dictionary of Physics and Chemistry, Third edition, Ryo Midorikawa/Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll,. as amended by later regulations of the project/intent combined process for the manufacture of epichlorohydrin (SPOLEK) Apr. 2005.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V; - 2005 p. 81/-8/5., vol. 5.

Klaus Weissermel, et al., "Industrial Organic Chemistry," ($3^{rd}$ Completely Revised Edition); VCH 1997. p. 93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997. p. 347-355.
Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).
Ullmann Encyl. Indust. Chem., $5^{th}$ Ed., vol. A6, (1988), pp. 401-477.
Polymer Science Dictionary, M.S.M., Elsevier Applied Chemistry, London and New York 1989, p. 86.
Perry's chemical Engineers' Handbook, Sixth Edition, Section 21, pp. 21-55.
Semendyava, N.D. et al., Khimicheskaya Promyshlennost, Seriya: Khornaya Promyshlennost (1981), 5, 21-2 (CA Summary) XP 002465275.
Rudnenko, E.V., et al., Kakokrasochnye Materialy I Ikh Primenenie (1988), 4, 69-71 (CA Summary) XP 002465276.
W. Giger et al., "14C/12C-Ratios in Organic Matter and Hydrocarbons Extracted from Dated Lake Sediments," Nuclear Instruments and Methods in Physics Research B5 (1984), 394-397. XP-002631954.
Jurgen O. Metzger, "Fats and Oils as Renewable Feedstock for Chemistry," Eur. J. Lipid Sci. Technol. (2009), 111, 865-876. XP-002631953.
Bruce M. Bell, "Glycerin as a Renewable Feedstock for Epichlorohydrin Production. The GTE Process," Clean-Soil, Air, Water, vol. 36, No. 8, (2008) pp. 657-661. XP-002631952.
Sang Hee Lee, et al., "Direct Preparation of Dichloropropanol (DCP) from Glycerol Using Heteropolyacid (HPA) Catalysts: A Catalyst Screen Study," Catalysis Communications (9), 2008, 1920-1923.
Myszkowski J. et al., "Removal of Chlorinated Organic Impurities from Hydrogen Chloride," CA, Jan. 1, 1900, XP002352444 (English CA Summary only).
Myszkowski J. et al., "Removal of Organic Compoiunds from Gaseous Hydrogen Chloride by an Absorption Method," CA, Jan. 1, 1900, XP002352445 (English CA summary only).
Milchert E. et al., "Recovering Hydrogen Chloride and Organic Chlor Compounds from the Reaction Mixture in the Chlorination of Ethylene," CA, Jan. 1, 1900, XP002352443 (English CA summary only).
Laine D.F., et al., "The Destruction of Organic Pollutants Under Mild Reaction Conditions ; A Review," Microchemical Journal, vol. 85, No. 2, 2006, pp. 183-193.
Rainwater Harvesting and Utilization, Internet Citation, XP003003726.
H. Galeman, Organic Synthesis, Section 1, pp. 234-235.
Chemical Encyclopedia 5, p. 457.
Epoxy Resins, Shanghai Resin Plant, Shangai People's Press, 1971.
Martinetti Richard et al., "Environment Le Recyclage De l'eau," Industrie Textile, Ste. Sippe Sarl, Metz, FR., No. 1300, Jul. 1, 1998, ISSN: 0019-9176.
Herman A. Bruson, et al., "Thermal Decomposition of Glyceryl Carbonates," Journal of the American Chemical Society, vol. 74, Apr. 1952 pp. 2100-2101.
M. Schellentrager, "Untersuchungen zur oxidation Entfarbung aus gewahlter Reaktivfarbstoffe: Analyse der Abbauprodukte miteels hochauflosender LC-MS", Diisertation, XP002548413 (Jan. 1, 2006) w/Attached English Abstract.
Azeotropic Data-III Compiled by Lee H. Horsley, The Dow Chemical Co., Midland, Mich., American Chemical Society (1973).
Yoshikazu Suzawa et al., Kagachu Sohchi (Chemical Apparatuses), vol. 23, No. 11, 3744, (published on Nov. 1981) with English translation.
Journal of American Oil Chemists' Society Jul. 1982, vol. 59, No. 7 pp. 292-295.
Chemical Engineering Handbook, 6th Revised Edition, 2nd print issued on Apr. 25, 2001, with attached English translation.
Organic synthesis, Part 1, published by Scientific Publishing, 1957.

Handbook of chemical products, organic chemical materials, Second edition, published by Chemical Industry Press, Jan. 1995.
R. A. Kiseleva and V.M. Goncharko, J. Appl. Chem. USSR, 1971, vol. 44, pp. 2086-2090.
Handbook of Corrosion data and material selection, published by Chemical Industry Press, edited by Jingyi Zuo, Yu Zuo; first edition, Oct. 1995 with attached English translation.
Handbook of azeotropic mixture, edited by information department of comprehensive scientific technology research institution of Fushun city, 1993.
Industry chemical reaction and application, pubished by Chinese Scientific Technology University Press, 1999 with attached English translation.
Epoxy resin, pubished by Shanghai People's Publishing House, 1971, with attached English translation.
Boschan and S. Winstein, Journal of the American Chemical Society, 1956, vol. 78, pp, 4921-4925.
Encyclopaedia for Chinese Adult Education, 1994, p. 623.
"Electrolytic cell test for electrolysis of epoxy sewage salt to prepare chlor-alkali", process Equipment Department of Research Institute of chlor-alkali, Shengyang chemical Plant, Liaononhg Chemical Industry, Issue n°2, pp. 32-37, published Dec. 31, 1981, with attached English translation.
"Analysis of the Composition of the Byproduct During the Manufacturing Process of Sepichlorhydrin by GC-MS", Ren Chengxin et al., Chemical Analysis and Measurement, vol. 12, Issue n° 3, p. 25-26, Dec. 31, 2003, with attached English translation.
Encyclopedia of Chemical Technology, vol. 5, Nov. 1993.
Manufacture and use of epoxy resin, edited by Shanghai Resin Factory, published by China Petrochemical Press, First Edition, Oct. 1974.
Fauconnier, "Preparation of Epichlorohydrin," Bull. Soc. Chim. Fr., No. 122, pp. 212-214 (With English Translation).
New Experimental Chemical Course 1, Basic Operation I, Section 4, Separation and Purification, pp. 251-252, Issued Sep. 20, 1975 (with English Translation).
Copyright Mar. 1992, Advanced Organic Chemistry, $4^{th}$ Ed., pp. 889, 908 and 937.
Yong, K.C., et al., "Refining of Crude Glycerine Recovered from Glycerol Residue by Simple Vacuum Distillation," Journal of Oil Palm Research, vol. 13, N°. 2, Dec. 2001, pp. 39-44.
Friedel et Silva, Bulletin de la Société Chimique de Paris, Arnnée 1873, 1er semestre—Nouvelle Série— Tome XIX, p. 98.
I.S. Neuberg, Biochemische Zeitshrift, 1930, vol. 221, pp. 492-493.
F. Krausz Ann. De Chimie, 12e série, t. Nov. 4-Dec. 1949, pp. 811-931.
Glycerin : An overview, Soap and Detergent Association. Copyright 1990 by the Soap and Detergent Association.
Chemical and Engineering News, 1948, 26 (38), pp. 2770-2771.
Fairbourn et al., "The Partial Esterification of Polyhydric Alcohols. Part XII. The Function of Ethylene-oxide Rings," J. Chem. Soc. 1932, pp. 1965-1972, Received, Apr. 6, 1932.
Clarke et al., Organic Syntheses, Coll., vol. 1, p. 233, (1941); vol. 3, p. 47, ( 1923).
Braun, Organic Syntheses, Coll., vol. 2, p. 256, (1943); vol. 6, p. 30, (1936).
Conant et al. Organic Syntheses, Coll., vol. 1, p. 292, (1941); vol. 2, p. 29, (1922).
Bull. Soc. Chim. Fr. (1943), 10, pp. 52-58, with English Translation.
"Chemical Properties and Derivatives of Glycerol", (1965), published by Glycerine Producers' Association in New York, pp. 1-20.
G.W. Busby and D.E. Gosvenor, "The Purification of Glycerin by Ion-Exchange," The Journal of The American Oil Chemists' Society, vol. 29, N°. 8, pp. 318-320 (1952).
L.L. Lamborn, "Modern Soaps, Candles and Glycerin," D. Van NOstrand Company, London, third edition 1918, pp. 542-550, 573-574.
G. Knothe, "Historical perspectives on vegetable oil-based diesel fuels", Inform, vol. 12, Nov. 2001. pp. 1103-1107.
U. Schuchardt et al., "Transesterification of Vegetable Oils: a Review," J. Braz. Chem. Soc., vol. 9, N°. 1, 199-210, 1998.
S. Claude, "Research of new outlets for glycerol—recent developemnts in France," Fett/Lipid 101 (1999), Nr. 3, S 101-104.

C.B. Prakash,"A critical review of Biodiesel as a Transportation Fuel in Canada," for the Transportation Systems Branch Air Pollution Prevention Directorate Enviornment Canada, Mar. 25, 1998, pp. 1-104.
H. Fukuda et al., "Biodiesel Fuel Production by transesterification of Oils", Journal of Bioscience and Bioengineering, vol. 92, No. 5, pp. 405-416 (2001).
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).
Armando Novelli, "The Preparation of Moni- and Dichlorohydrins of Glycerol," Anal. Farm. Bioquim, vol. 1, 1930, pp. 8-19 (with English Abstract).
Derwent Publications, AN 109:6092 CA, JP 62-242638 (Oct. 23, 1987).
Derwent Publications, AN 1987-338139 [48], JP 62-242638, (Oct. 23, 1987).
J.B. Conant et al., "Glycerol a,y-Dichlorophydrin," Organic Syntheses Coll., vol. 1, p. 292, 1941.
I. Miyakawa et al., Nagoya Sangyo Kagaku Kenkyusho Kenkyu Hokoku, 10, 49-52 (1957).
Han Xiu-Ying et al., Shanxi Daxue Xueba Bianjibu, 2002, 25(4), 379-80).
Gibson., "The Preparation, Properties, and Uses of Glycerol Derivatives. Part III. The Chlorohydrins", Chemistry and Industry, Chemical Society, pp. 949-975, 1931.
Carre et al., "La Transformation Des Alcools Polyatomiques En Mono-Et En Polychlorhydrines Au Moyen Du Chlorure De Thionyle", Bull. Soc. Chim. Fr., No. 49, pp. 1150-1154, 1931.
Fauconnier, "Preparation De L'Epichlorhydrine", Bull. Soc. Chim. Fr., No. 50, pp. 212-214, 1888.
Bonner et al., "The Composition of Constant Boiling Hydrochloric Acid At Pressures of 50 to 1220 Millimeters", Journal of American Chemical Society, vol. 52, pp. 633-635, 1930.
U.S. Appl. No. 11/914,879, filed Nov. 19, 2007, Gilbeau.
U.S. Appl. No. 11/915,059, filed Nov. 20, 2007, Gilbeau, et al.
U.S. Appl. No. 11/914,836, filed Nov. 19, 2007, Krafft, et al.
U.S. Appl. No. 11/915,067, filed Nov. 20, 2007, Krafft, et al.
U.S. Appl. No. 11/914,874, filed Nov. 19, 2007, Krafft, et al.
U.S. Appl. No. 11/914,862, filed Nov. 19, 2007, Gilbeau.
U.S. Appl. No. 11/914,856, filed Nov. 19, 2007, Krafft, et al.
U.S. Appl. No. 11/915,046, filed Nov. 20, 2007, Krafft, et al.
U.S. Appl. No. 11/914,891, filed Nov. 19, 2007, Krafft, et al.
U.S. Appl. No. 11/915,056, filed Nov. 20, 2007, Gilbeau.
U.S. Appl. No. 11/915,053, filed Nov. 20, 2007, Gilbeau.
U.S. Appl. No. 11/915,088, filed Nov. 20, 2007, Krafft, et al.
U.S. Appl. No. 60/560,676, filed Apr. 8, 2004, Unknown.
U.S. Appl. No. 60/734,659, filed Nov. 8, 2005, Unknown.
U.S. Appl. No. 60/734,627, filed Nov. 8, 2005, Unknown.
U.S. Appl. No. 60/734,657, filed Nov. 8, 2005, Unknown.
U.S. Appl. No. 60/734,658, filed Nov. 8, 2005, Unknown.
U.S. Appl. No. 60/734,635, filed Nov. 8, 2005, Unknown.
U.S. Appl. No. 60/734,634, filed Nov. 8, 2005, Unknown.
U.S. Appl. No. 60/734,637, filed Nov. 8, 2005, Unknown.
U.S. Appl. No. 60/734,636, filed Nov. 8, 2005, Unknown.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Unknown.
U.S. Appl. No. 12/304,391, filed Dec. 11, 2008, Krafft, et al.
U.S. Appl. No. 13/060,421, filed Feb. 23, 2011, Balthasart, et al.
U.S. Appl. No. 13/051,007, filed Mar. 18, 2011, Krafft, et al.
U.S. Appl. No. 13/063,230, filed Mar. 10, 2011, Krafft, et al.
U.S. Appl. No. 12/681,083, filed Mar. 31, 2010, Bobet, et al.
U.S. Appl. No. 12/529,777, filed Sep. 3, 2009, Krafft, et al.

U.S. Appl. No. 12/529,778, filed Sep. 3, 2009, Krafft, et al.
U.S. Appl. No. 12/935,538, filed Sep. 29, 2010, Gilbeau, et al.
U.S. Appl. No. 12/864,211, filed Jul. 27, 2010, Gilbeau, et al.
U.S. Appl. No. 12/663,753, filed Dec. 9, 2009, Krafft, et al.
U.S. Appl. No. 12/663,744, filed Dec. 9, 2009, Boulos, et al.
U.S. Appl. No. 12/663,749, filed Dec. 9, 2009, Krafft, et al.
U.S. Appl. No. 12/663,887, filed Dec. 10, 2009, Krafft, et al.
U.S. Appl. No. 12/502,296, filed Jul. 9, 2009, Krafft, et al.

U.S. Appl. No. 12/502,342, filed Jul. 14, 2009, Krafft, et al.
U.S. Appl. No. 12/527,538, filed Aug. 17, 2009, Gilbeau, et al.
U.S. Appl. No. 12/600,018, filed Nov. 13, 2009, Borremans, et al.
U.S. Appl. No. 13/131,516, filed May 26, 2011, Gilbeau, et al.
U.S. Appl. No. 13/238,206, filed Sep. 21, 2011, Gilbeau, et al.
U.S. Appl. No. 12/745,802, filed Jun. 2, 2010, Gilbeau, et al.

\* cited by examiner

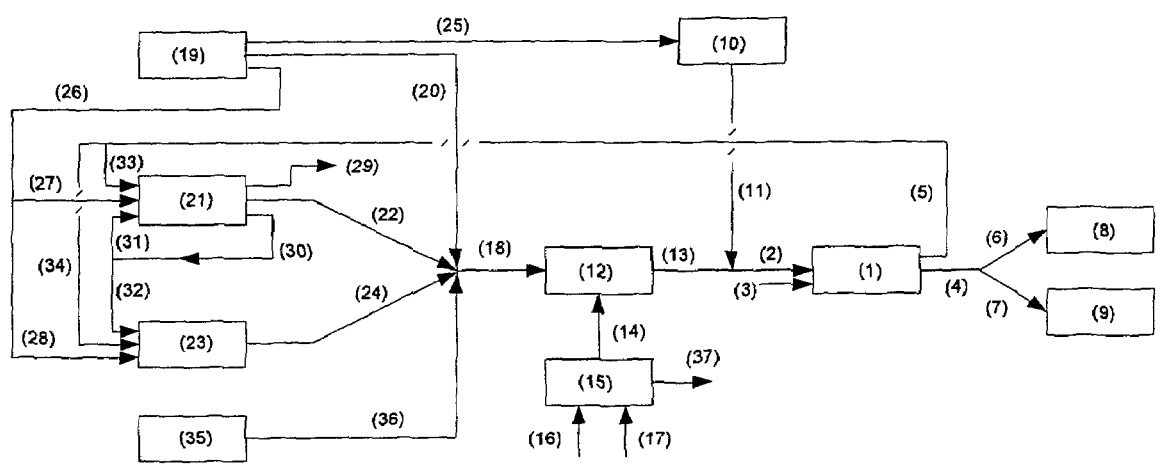

METHOD FOR MAKING A CHLORHYDRINE BY REACTION BETWEEN A POLYHYDROXYLATED ALIPHATIC HYDROCARBON AND A CHLORINATING AGENT

The present patent application is a 371 of PCT/EP2006/062448, filed May 19, 2006. This application also claims the benefit of patent application FR 05.05120 and of patent application EP 05104321.4, both filed on 20 May 2005, and of provisional U.S. patent applications 60/734,659, 60/734,627, 60/734,657, 60/734,658, 60/734,635, 60/734,634, 60/734,637 and 60/734,636, all filed on 8 Nov. 2005, the content of all of which is incorporated here by reference.

The present invention relates to a process for preparing a chlorohydrin. It relates more specifically to a process for preparing a chlorohydrin from a polyhydroxylated aliphatic hydrocarbon and a chlorinating agent.

Chlorohydrins are reaction intermediates in the preparation of epoxides. Dichloropropanol, for example, is a reaction intermediate in the preparation of epichlorohydrin and of epoxy resins (Kirk-Othmer Encyclopedia of Chemical Technology, Fourth Edition, 1992, Vol. 2, page 156, John Wiley & Sons, Inc.).

According to known processes it is possible to obtain dichloropropanol in particular by hypochlorinating allyl chloride, by chlorinating allyl alcohol and by hydrochlorinating glycerol. This latter process has the advantage that the dichloropropanol can be obtained starting from fossil raw materials or from renewable raw materials, and it is known that natural petrochemical resources, from which the fossil materials are obtained, such as petroleum, natural gas or coal, for example, are limited in their terrestrial availability.

International application WO 2005/021476 and application WO 2005/054167 of SOLVAY SA describe a process for preparing dichloropropanol by reacting glycerol with hydrogen chloride. The hydrogen chloride may be gaseous or in the form of aqueous solutions.

The toxicity and the corrosiveness of these compounds complicate their preparation, purification, storage and transportation. Hydrogen chloride is toxic by contact, inhalation and ingestion (The Merck Index, Eleventh Edition, 1989, page 759). It is typically transported in the form of liquefied gas in pressurized containers. Aqueous hydrochloric acid is extremely corrosive (The Merck Index, Eleventh Edition, 1989, page 756) and requires apparatus made of special materials for its storage and its transportation. These drawbacks are disadvantageous to the processes for preparing organic chlorine products that make use of these chlorinating agents in one of their steps.

The aim of the invention is to provide a process for preparing chlorohydrin from a polyhydroxylated aliphatic hydrocarbon, an ester of a polyhydroxylated aliphatic hydrocarbon or a mixture thereof, and a chlorinating agent, which does not exhibit these drawbacks.

The invention accordingly provides a process for preparing a chlorohydrin from a polyhydroxylated aliphatic hydrocarbon, from an ester of a polyhydroxylated aliphatic hydrocarbon or from a mixture thereof, and from a chlorinating agent, the chlorinating agent comprising at least one of the following compounds: nitrogen, oxygen, hydrogen, chlorine, an organic hydrocarbon compound, an organic halogen compound, an organic oxygen compound and a metal.

It has been found, surprisingly, that at least partly supplying the process for preparing chlorohydrin with a chlorinating agent comprising these compounds gives particularly good results. In particular the yield of the process for preparing the chlorohydrin is not adversely affected by the use of this chlorinating agent.

In the process according to the invention the organic hydrocarbon compound is selected from saturated and unsaturated aliphatic and aromatic hydrocarbons and mixtures thereof.

In the process according to the invention the unsaturated aliphatic hydrocarbon is selected from acetylene, ethylene, propylene, butene, propadiene, methylacetylene and mixtures thereof, the saturated aliphatic hydrocarbon is selected from methane, ethane, propane, butane and mixtures thereof and the aromatic hydrocarbon is benzene.

In the process according to the invention the organic halogen compound is an organic chlorine compound selected from chloromethanes, chloroethanes, chloropropanes, chlorobutanes, vinyl chloride, vinylidene chloride, monochloropropenes, perchloroethylene, trichloroethylene, chlorobutadienes, chlorobenzenes and mixtures thereof.

In the process according to the invention the organic halogen compound is an organic fluorine compound selected from fluoromethanes, fluoroethanes, vinyl fluoride, vinylidene fluoride and mixtures thereof.

In the process according to the invention the organic oxygen compound is selected from alcohols, chloroalcohols, chloroethers and mixtures thereof.

In the process according to the invention the metal is selected from alkali metals, alkaline earth metals, iron, nickel, copper, lead, arsenic, cobalt, titanium, cadmium, antimony, mercury, zinc, selenium, aluminium, bismuth and mixtures thereof.

In the process according to the invention the chlorinating agent is obtained at least partly from a process for preparing allyl chloride and/or a process for preparing chloromethanes and/or a process of chlorinolysis and/or a process for oxidizing chlorine compounds at a temperature greater than or equal to 800° C.

The preparation processes may be carried out independently in batch mode or in continuous mode. It is preferred for at least one of the processes to be carried out in continuous mode. It is preferred more particularly for the continuous mode to be used for all of the preparation processes under consideration.

In the process according to the invention the chlorinating agent comprises hydrogen chloride.

The term "polyhydroxylated aliphatic hydrocarbon" refers to a hydrocarbon which contains at least two hydroxyl groups attached to two different saturated carbon atoms. The polyhydroxylated aliphatic hydrocarbon may contain, but is not limited to, from 2 to 60 carbon atoms.

Each of the carbons of a polyhydroxylated aliphatic hydrocarbon bearing the hydroxyl functional group (OH) cannot possess more than one OH group and must have sp3 hybridization. The carbon atom carrying the OH group may be primary, secondary or tertiary. The polyhydroxylated aliphatic hydrocarbon used in the present invention must contain at least two sp3-hybridized carbon atoms carrying an OH group. The polyhydroxylated aliphatic hydrocarbon includes any hydrocarbon containing a vicinal diol (1,2-diol) or a vicinal triol (1,2,3-triol), including the higher, vicinal or contiguous orders of these repeating units. The definition of the polyhydroxylated aliphatic hydrocarbon also includes, for example, one or more 1,3-, 1,4-, 1,5- and 1,6-diol functional groups. The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic moieties or heteroatoms, including, for example, heteroatoms of halogen, sulphur, phosphorus, nitrogen, oxygen, silicon and boron type, and mixtures thereof.

Polyhydroxylated aliphatic hydrocarbons which can be used in the present invention comprise, for example, 1,2-ethanediol (ethylene glycol), 1,2-propane-diol (propylene glycol), 1,3-propanediol, 1-chloro-2,3-propanediol (chloropropanediol), 2-chloro-1,3-propanediol (chloropropanediol), 1,4-butanediol, 1,5-pentanediol, cyclohexanediols, 1,2-butanediol, 1,2-cyclo-hexanedimethanol, 1,2,3-propanetriol (also known as "glycerol" or "glycerin"), and mixtures thereof. With preference the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two thereof. More preferably the polyhydroxylated aliphatic hydrocarbon used in the present invention includes, for example, 1,2-ethanediol, 1,2-propanediol, chloropropanediol and 1,2,3-propanetriol, and mixtures of at least two thereof. 1,2,3-Propanetriol or glycerol is the most preferred.

The esters of the polyhydroxylated aliphatic hydrocarbon may be present in the polyhydroxylated aliphatic hydrocarbon and/or may be produced in the process for preparing the chlorohydrin and/or may be prepared prior to the process for preparing the chlorohydrin. Examples of esters of the polyhydroxylated aliphatic hydrocarbon comprise ethylene glycol monoacetate, propanediol monoacetates, glycerol monoacetates, glycerol monostearates, glycerol diacetates and mixtures thereof.

The term "chlorohydrin" is used here in order to describe a compound containing at least one hydroxyl group and at least one chlorine atom attached to different saturated carbon atoms. A chlorohydrin which contains at least two hydroxyl groups is also a polyhydroxylated aliphatic hydrocarbon. Accordingly the starting material and the product of the reaction may each be chlorohydrins. In that case the "product" chlorohydrin is more chlorinated than the starting chlorohydrin, in other words has more chlorine atoms and fewer hydroxyl groups than the starting chlorohydrin. Preferred chlorohydrins are chloroethanol, chloropropanol, chloropropanediol, dichloropropanol and mixtures of at least two thereof. Dichloropropanol is particularly preferred. Chlorohydrins which are more particularly preferred are 2-chloroethanol, 1-chloropropan-2-ol, 2-chloropropan-1-ol, 1-chloropropane-2,3-diol, 2-chloropropane-1,3-diol, 1,3-dichloropropan-2-ol, 2,3-dichloropropan-1-ol and mixtures of at least two thereof.

The polyhydroxylated aliphatic hydrocarbon, the ester of polyhydroxylated aliphatic hydrocarbon, or the mixture thereof in the process according to the invention may be obtained starting from fossil raw materials or starting from renewable raw materials, preferably starting from renewable raw materials.

By fossil raw materials are meant materials obtained from the processing of petrochemical natural resources, such as petroleum, natural gas and coal, for example. Among these materials preference is given to organic compounds containing 2 and 3 carbon atoms. When the polyhydroxylated aliphatic hydrocarbon is glycerol, allyl chloride, allyl alcohol and "synthetic" glycerol are particularly preferred. By "synthetic" glycerol is meant a glycerol generally obtained from petrochemical resources. When the polyhydroxylated aliphatic hydrocarbon is ethylene glycol, ethylene and "synthetic" ethylene glycol are particularly preferred. By "synthetic" ethylene glycol is meant an ethylene glycol generally obtained from petrochemical resources. When the polyhydroxylated aliphatic hydrocarbon is propylene glycol, propylene and "synthetic" propylene glycol are particularly preferred. By "synthetic" propylene glycol is meant a propylene glycol generally obtained from petrochemical resources.

By renewable raw materials are meant materials obtained from the processing of renewable natural resources. Among these materials preference is given to "natural" ethylene glycol, "natural" propylene glycol and "natural" glycerol. "Natural" ethylene glycol, propylene glycol and glycerol are obtained for example by conversion of sugars by thermochemical processes, it being possible for these sugars to be obtained starting from biomass, as described in "Industrial Bioproducts: Today and Tomorrow", Energetics, Incorporated for the U.S. Department of Energy, Office of Energy Efficiency and Renewable Energy, Office of the Biomass Program, July 2003, pages 49, 52 to 56. One of these processes is, for example, the catalytic hydrogenolysis of sorbitol obtained by thermochemical conversion of glucose. Another process is, for example, the catalytic hydrogenolysis of xylitol obtained by hydrogenation of xylose. The xylose may for example be obtained by hydrolysis of the hemicellulose present in maize fibres. By "natural glycerol" or "glycerol obtained from renewable raw materials" is meant, in particular, glycerol obtained during the production of biodiesel or else glycerol obtained during conversions of animal or vegetable oils or fats in general, such as saponification, transesterification or hydrolysis reactions.

Among the oils which can be used to prepare natural glycerol, mention may be made of all common oils, such as palm oil, palm kernel oil, copra oil, babassu oil, former or new (low erucic acid) colza oil, sunflower oil, maize oil, castor oil and cotton oil, peanut oil, soya bean oil, linseed oil and crambe oil, and all oils obtained, for example, from sunflower plants or colza plants obtained by genetic modification or hybridization.

It is also possible to employ used frying oils, various animal oils, such as fish oils, tallow, lard and even squaring greases.

Among the oils used mention may also be made of oils which have been partly modified by means, for example, of polymerization or oligomerization, such as, for example, the "stand oils" of linseed oil and of sunflower oil, and blown vegetable oils.

A particularly suitable glycerol may be obtained during the conversion of animal fats. Another particularly suitable glycerol may be obtained during the production of biodiesel. A third, very suitable glycerol may be obtained during the conversion of animal or vegetable oils or fats by transesterification in the presence of a heterogeneous catalyst, as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and the heterogeneous catalyst is employed in the form of a fixed bed. This latter process can be a process for producing biodiesel.

In the process for preparing a chlorohydrin according to the invention, the polyhydroxylated aliphatic hydrocarbon, the ester of polyhydroxylated aliphatic hydrocarbon or the mixture thereof may be as described in the patent application entitled "Process for preparing chlorohydrin by converting polyhydroxylated aliphatic hydrocarbons", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of a polyhydroxylated aliphatic hydrocarbon or a mixture thereof whose total metal content, expressed in elemental form, is greater than or equal to 0.1 µg/kg and less than or equal to 1000 mg/kg is reacted with a chlorinating agent.

In the process according to the invention it is preferred to use glycerol obtained starting from renewable raw materials.

The process for preparing chlorohydrins according to the invention can be followed by the preparation of an epoxide.

The term "epoxide" is used herein to describe a compound containing at least one oxygen bridged on a carbon-carbon bond. Generally speaking, the carbon atoms of the carbon-carbon bond are adjacent and the compound may contain atoms other than carbon atoms and oxygen atoms, such as hydrogen atoms and halogens. The preferred epoxides are ethylene oxide, propylene oxide, glycidol, epichlorohydrin and mixtures of at least two thereof.

The process for preparing the epoxide may be followed by a process for preparing epoxy resins.

The processes from which the chlorinating agent may have come are often combined. The heavy by-products of the synthesis of allyl chloride and epichlorohydrin are advantageously employed as a source of raw materials in a high-temperature chlorinolysis process for producing materials which are utilized commercially. These plants may, however, have other sources of raw materials. Oxidation at a temperature of greater than or equal to 800° C. is used in order to remove organic chlorine or oxygen wastes.

The processes from which the chlorinating agent may have come generate hydrogen chloride or aqueous solutions of hydrogen chloride as a co-product. These acids are generally mediocre in quality, containing traces of organic substances. They are advantageously employed in the abovementioned process for preparing chlorohydrin either as they are or after treatment.

It has been found, surprisingly, that at least partly supplying the process for preparing chlorohydrin with the crude chlorinating agent obtained as it is in these preparation processes gives particularly good results. In particular, the yield of the process for preparing the chlorohydrin is not adversely affected by the use of this unprocessed chlorinating agent.

Furthermore, at least partly supplying the chlorohydrin preparation process with the chlorinating agent obtained from a process for preparing allyl chloride and/or a process of chlorinolysis and/or a process for preparing chloromethane and/or a process for oxidizing chlorine compounds at a temperature greater than or equal to 800° C., as well as limiting transportation of dangerous materials, with removal of the costs associated with such transportation, allows an advantageous alternative utilization of the acids co-produced in these processes. Moreover, sharing plant between different processes for preparing a single product may be considered, which likewise contributes to a reduction in the costs of these processes.

In the process for preparing a chlorohydrin according to the invention, the polyhydroxylated aliphatic hydrocarbon, the ester of polyhydroxylated aliphatic hydrocarbon or the mixture thereof may be a crude product or a purified product, such as are specifically disclosed in application WO 2005/054167 of SOLVAY SA, from page 2 line 8 to page 4 line 2. In the process for preparing a chlorohydrin according to the invention, the polyhydroxylated aliphatic hydrocarbon, the ester of polyhydroxylated aliphatic hydrocarbon or the mixture thereof may have an alkali metal and/or alkaline earth metal content of less than or equal to 5 g/kg, as described in the application entitled "Process for preparing a chlorohydrin by chlorinating a polyhydroxylated aliphatic hydrocarbon", filed in the name of SOLVAY SA on the same day as the present application, and whose content is incorporated here by reference. The alkali metals may be selected from lithium, sodium, potassium, rubidium and cesium and the alkaline earth metals may be selected from magnesium, calcium, strontium and barium.

In the process according to the invention, the alkali metal and/or alkaline earth metal content of the polyhydroxylated aliphatic hydrocarbon, the ester of polyhydroxylated aliphatic hydrocarbon or the mixture thereof is less than or equal to 5 g/kg, often less than or equal to 1 g/kg, more particularly less than or equal to 0.5 g/kg and in certain cases less than or equal to 0.01 g/kg. The alkali metal and/or alkaline earth metal content of the glycerol is generally greater than or equal to 0.1 µg/kg.

In the process according to the invention the alkali metals are generally lithium, sodium, potassium and cesium, often sodium and potassium, and frequently sodium.

In the process for preparing a chlorohydrin according to the invention, the lithium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the sodium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the potassium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the rubidium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the cesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention the alkaline earth metal elements are generally magnesium, calcium, strontium and barium, often magnesium and calcium and frequently calcium.

In the process according to the invention, the magnesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the calcium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the strontium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the barium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention the alkali and/or alkaline earth metals are generally present in the form of salts, frequently in the form of chlorides, sulphates and mixtures thereof. Sodium chloride is the most often encountered.

In the process for preparing a chlorohydrin according to the invention, the chlorinating agent may be as described in application WO 2005/054167 of SOLVAY SA, from page 4 line 25 to page 6 line 2.

In the process for preparing a chlorohydrin according to the invention, the chlorinating agent may be hydrogen chloride as described in application WO 2005/054167 of SOLVAY SA, from page 4 line 30 to page 6 line 2.

In one advantageous embodiment of the process for preparing a chlorohydrin according to the invention, the chlorinating agent is gaseous hydrogen chloride or an aqueous solution of hydrogen chloride, or a combination of the two.

This chlorinating agent is particularly advantageous, since it is often obtained as a by-product in organic synthesis in chlorination, elimination or substitution, or else by combustion. The present invention allows this by-product to be utilized.

In a first embodiment of the process according to the invention, the chlorinating agent originates at least partly from a process for preparing allyl chloride.

In a first version of this first embodiment, the allyl chloride may be obtained by chlorinating propylene. In that case the process for preparing allyl chloride is supplied with at least propylene and chlorine. Other compounds may also be present in the feedstock, such as, for example, non-chlorinated hydrocarbons other than propylene, partially chlorinated hydrocarbons, totally chlorinated hydrocarbons or mixtures thereof.

In a second version of this first embodiment, the allyl chloride may be obtained by dehydrochlorination of dichloropropane. In that case the process for preparing allyl chloride is supplied with, at least, partially chlorinated hydrocarbons, preferably containing dichloropropane, especially 1,2-dichloro-propane.

A description of processes for preparing allyl chloride may be found in the reference work "Ullmann's Encyclopedia of Industrial Chemistry, Fifth, Completely Revised Edition, 1985, Volume A1, pages 427-429".

In a second embodiment of the process according to the invention, the chlorinating agent originates at least partly from a process for preparing chloromethanes.

In this second embodiment the preparation process is supplied with methane and/or methyl chloride and chlorine. The chlorination process may be thermal, photochemical or catalytic. Thermal and photochemical processes are preferred.

A description of processes for preparing chloromethanes may be found in the reference work "Ullmann's Encyclopedia of Industrial Chemistry, Fifth, Completely Revised Edition, 1986, Volume A6, pages 240-252".

In a third embodiment of the process according to the invention, the chlorinating agent originates at least partly from a chlorinolysis process. Chlorinolysis refers to any chlorine-mediated decomposition reaction and more particularly to decomposition reactions of organic compounds that are carried out at temperatures greater than or equal to 300° C., preferably greater than or equal to 350° C. In this third embodiment the chlorinolysis process is supplied with at least chlorine and saturated or unsaturated aliphatic or aromatic hydrocarbons, preferably aliphatic hydrocarbons, selected from non-chlorinated aliphatic hydrocarbons containing 1 to 6 carbon atoms, partially and/or fully chlorinated aliphatic hydrocarbons containing 1 to 6 carbon atoms and 1 to 14 chlorine atoms, and mixtures thereof. Non-chlorinated hydrocarbons are for example propane, propylene, methylacetylene, methane and ethylene. Partially chlorinated hydrocarbons are for example chloroform, trichloropropanes, chloropropenes, tetrachloroethanes, trichloroethanes, acetylene chloride and tetrachloropentanes. Fully chlorinated hydrocarbons may be selected from carbon tetrachloride, hexachloroethane and perchloroethylene. One example of such a process is the process for pyrolysing chlorinated hydrocarbons containing from one to three carbon atoms in the presence of chlorine in order to produce perchloroethylene and carbon tetrachloride. Generally speaking, these hydrocarbons contain no heteroatoms other than chlorine.

A description of chlorinolysis processes may be found in the reference work "Propylene and its Industrial Derivatives, Hancock E. G., 1973, pages 298-332".

In a fourth embodiment of the process according to the invention, the chlorinating agent originates at least partly from a process for oxidizing chlorine compounds at a temperature greater than or equal to 800° C. This temperature is often greater than or equal to 900° C. and more particularly greater than or equal to 1000° C. This process will be referred to hereinbelow as the high-temperature oxidation process; in this embodiment, the oxidation process is supplied with at least one oxidizing agent and at least one chlorine compound.

In this fourth embodiment the oxidizing agent may be selected from oxygen, chlorine oxides, nitrogen oxides, mixtures thereof and mixtures thereof with nitrogen. Water may be usefully added to the oxidizing agent in particular in order to facilitate the oxidation of chlorine compounds.

In this fourth embodiment, the chlorine compounds may be organic or inorganic compounds. Organic chlorine compounds are preferred. These organic chlorine compounds are hydrocarbons selected from partially chlorinated hydrocarbons containing 1 to 10 carbon atoms and 1 to 21 chlorine atoms, fully chlorinated hydrocarbons containing 1 to 4 carbon atoms, and mixtures thereof.

One example of a process of this kind for oxidizing chlorine compounds is that in which organic chlorine and oxygen compounds are oxidized in the form of carbon dioxide. In a process of this kind, chlorine compounds obtained from processes for preparing allyl chloride, epichlorohydrin, dichloroethane, propylene oxide, vinylidene chloride, vinyl chloride, 1,1,1-trichloroethane, chloromethanes, trichloroethylene and a chlorinolysis process are oxidized at high temperature, thereby making it possible to utilize the energy content of the chlorine compounds in the form of $CO_2$ and generating hydrogen chloride in the form of aqueous solutions of hydrogen chloride ("technical" hydrochloric acid), which can be purified or non-purified.

A description of high-temperature oxidation processes may be found in the reference work "Ullmann's Encyclopedia of Industrial Chemistry, Fifth, Completely Revised Edition, 1985, Volume A13, pages 292-293".

In a first preferred aspect of the process according to the invention, the chlorinating agent obtained from a process for preparing allyl chloride and/or a process for preparing chloromethanes and/or a chlorinolysis process and/or a high-temperature oxidation process and which supplies the preparation of dichloropropanol comprises liquid or gaseous hydrogen chloride, preferably gaseous hydrogen chloride. With particular preference the hydrogen chloride is substantially anhydrous. "Substantially anhydrous" hydrogen chloride means hydrogen chloride whose water content is generally less than or equal to 15 mol %, preferably less than or equal to 10 mol % and with particular preference less than or equal to 8 mol %. This water content is generally greater than or equal to 0.01 ppm by mole.

In this first aspect of the process according to the invention, the nitrogen content of the chlorinating agent is generally greater than or equal to 0.1 ppm by volume, often greater than or equal to 10 ppm by volume and in particular greater than or equal to 20 ppm by volume. This content is generally less than or equal to 50 000 ppm by volume, often less than or equal to 40 000 ppm by volume and in particular less than or equal to 30 000 ppm by volume.

In this first aspect of the process according to the invention, the oxygen content of the chlorinating agent, not taking account of the water and nitrogen present in the chlorinating agent, is generally greater than or equal to 0.1 ppm by volume and often greater than or equal to 0.5 ppm by volume. This content is generally less than or equal to 5% by volume, often less than or equal to 2% by volume and in particular less than or equal to 1% by volume.

In this first aspect of the process according to the invention, the hydrogen content of the chlorinating agent, not taking account of the water and nitrogen present in the chlorinating agent, is generally greater than or equal to 0.1 ppm by volume and often greater than or equal to 0.5 ppm by volume. This content is generally less than or equal to 0.1% by volume and often less than or equal to 500 ppm by volume.

In this first aspect of the process according to the invention, the chlorine content of the chlorinating agent, not taking account of the water and nitrogen present in the chlorinating agent, is generally greater than or equal to 0.1 ppm by volume and often greater than or equal to 0.5 ppm by volume. This content is generally less than or equal to 2000 ppm by volume, often less than or equal to 1000 ppm by volume and in particular less than or equal to 500 ppm by volume.

In this first aspect of the process according to the invention, the methane content of the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This content is generally less than or equal to 10 000 ppm by volume, often less than or equal to 5000 ppm by volume and in particular less than or equal to 4000 ppm by volume.

In this first aspect of the process according to the invention, the carbon monoxide content of the chlorinating agent, not taking account of the water and nitrogen present in the chlorinating agent, is generally greater than or equal to 0.1 ppm by volume, often greater than or equal to 0.5 ppm by volume and in particular greater than or equal to 1 ppm by volume. This content is generally less than or equal to 10 000 ppm by volume, often less than or equal to 5000 ppm by volume and in particular less than or equal to 4000 ppm by volume.

In this first aspect of the process according to the invention, the carbon dioxide content of the chlorinating agent, not taking account of the water and nitrogen present in the chlorinating agent, is generally greater than or equal to 0.1 ppm by volume, often greater than or equal to 0.5 ppm by volume and in particular greater than or equal to 1 ppm by volume. This content is generally less than or equal to 10 000 ppm by volume, often less than or equal to 5000 ppm by volume and in particular less than or equal to 4000 ppm by volume.

In this first aspect of the process according to the invention, the overall amount of organic chlorine products such as, for example, chloromethanes, ethyl chloride, dichloroethane, vinyl chloride and chlorobenzene in the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This amount is generally less than or equal to 50 000 ppm by volume, often less than or equal to 20 000 ppm by volume and in particular less than or equal to 10 000 ppm by volume.

In this first aspect of the process according to the invention, the overall amount of organic non-chlorinated products such as, for example, ethylene, acetylene, ethane, propylene, methylacetylene and propane in the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This amount is generally less than or equal to 50 000 ppm by volume, often less than or equal to 20 000 ppm by volume and in particular less than or equal to 10 000 ppm by volume.

In this first aspect of the process according to the invention, the overall amount of organic fluorine products such as, for example, vinyl fluoride, fluoroethane, vinylidene fluoride and fluoromethanes in the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This amount is generally less than or equal to 500 ppm by volume, often less than or equal to 20 000 ppm by volume and in particular less than or equal to 10 000 ppm by volume.

In this first aspect of the process according to the invention, the overall amount of organic products containing heteroatoms other than chlorine and fluorine such as, for example, alcohols and acids in the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This amount is generally less than or equal to 50 000 ppm by volume, often less than or equal to 20 000 ppm by volume and in particular less than or equal to 10 000 ppm by volume.

In this first aspect of the process according to the invention, the propylene content of the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This amount is generally less than or equal to 15 000 ppm by volume, often less than or equal to 10 000 ppm by volume and in particular less than or equal to 5000 ppm by volume.

In this first aspect of the process according to the invention, the monochloropropene content of the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This amount is generally less than or equal to 5000 ppm by volume, often less than or equal to 1000 ppm by volume and in particular less than or equal to 500 ppm by volume.

In this first aspect of the process according to the invention, the sum of the amounts of chloropropane in the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This amount is generally less than or equal to 10 000 ppm by volume, often less than or equal to 4000 ppm by volume and in particular less than or equal to 3000 ppm by volume.

In this first aspect of the process according to the invention, the amount of isopropanol, chloroalcohols and chloroethers in the chlorinating agent, not taking account of the water and nitrogen present in the chlorinating agent, is generally greater than or equal to 0.1 ppm by volume, often greater than or equal to 1 ppm by volume and in particular greater than or equal to 5 ppm by volume. This amount is generally less than or equal to 5000 ppm by volume, often less than or equal to 4000 ppm by volume and in particular less than or equal to 3000 ppm by volume.

In a second preferred aspect of the process according to the invention, the hydrogen chloride is an aqueous solution of hydrogen chloride. In this case the hydrogen chloride content of the solution is generally at least 10% by weight. Preferably this content is greater than or equal to 15% by weight. In this case the hydrogen chloride content of the solution is generally not more than 37% by weight.

This second aspect allows the utilization of aqueous solutions of hydrogen chloride that are of low quality, obtained for example from the pyrolysis of organic chlorine compounds or having been used for the pickling of metals.

In a first version of this second aspect, a concentrated aqueous solution of hydrogen chloride, containing generally from 28% to 37% by weight of hydrogen chloride, is used as the primary source of the chlorinating agent and the said concentrated solution is separated, by evaporation for example, into at least two fractions, the first being composed essentially of anhydrous hydrogen chloride and the second containing hydrogen chloride and water in proportions in which they form an azeotrope, the said azeotrope being composed, at a pressure of 101.3 kPa, of 19% to 25% of hydrogen chloride and of 75% to 81% by weight of water, in particular of approximately 20% by weight of hydrogen chloride and approximately 80% of water. The 20% aqueous hydrogen chloride solution may optionally be employed to absorb the hydrogen chloride produced by the process for preparing allyl chloride, the chlorinolysis process, the process for preparing chloromethane and the high-temperature oxidation process, so as to generate an aqueous hydrogen chloride solution containing 33% by weight of hydrogen chloride.

When an aqueous solution of hydrogen chloride is used as chlorinating agent, this aspect allows the use of a chlorinating agent which is easy to transport while at the same time allowing effective control of the water content of the reaction medium, especially when the reaction between glycerol and the chlorinating agent is carried out in two or more steps.

The aqueous solution of hydrogen chloride which is used in this second aspect of the process according to the invention may comprise compounds other than water and hydrogen chloride. These compounds may among others be inorganic chlorine or non-chlorine compounds and saturated or unsaturated non-chlorine, partially chlorinated or fully chlorinated organic compounds. These compounds may differ as a function of the preparation process from which the aqueous hydrogen chloride solution has come.

In this second aspect of the process according to the invention, the amounts of oxygen, hydrogen, chlorine, methane, carbon monoxide, carbon dioxide, organic chlorine compounds, organic non-chlorine compounds, organic fluorine compounds, organic compounds containing heteroatoms other than chlorine and fluorine, of propylene, monochloropropenes, chloropropanes, isopropanol, chloroalcohols and chloroethers in the chlorinating agent, not taking account of the water present in the chlorinating agent, are identical to the values given above for the first aspect of the process according to the invention.

In this second aspect of the process according to the invention, the individual amounts of metals, and in particular of alkali metals, alkaline earth metals, iron, nickel, copper, lead, arsenic, cobalt, titanium, cadmium, antimony, mercury, zinc, selenium, aluminium and bismuth are generally greater than or equal to 0.03 ppb by weight, often greater than or equal to 0.3 ppb by weight and frequently greater than 1 ppb by weight. These amounts are generally less than or equal to 5 ppm by weight and preferably less than or equal to 1 ppm by weight.

In the process according to the invention, the fraction of chlorinating agent which supplies the preparation of dichloropropanol and which has come from a process for preparing allyl chloride and/or a chlorinolysis process and/or a process for preparing chloromethane and/or a high-temperature oxidation process is generally greater than or equal to 0% by weight of the chlorinating agent, often greater than or equal to 10% by weight and frequently greater than or equal to 20% by weight. This fraction is generally less than or equal to 100% by weight of the chlorinating agent, often less than or equal to 90% by weight and frequently less than 80% by weight.

In the process for preparing an organic chlorine product according to the invention, the reaction of the polyhydroxylated aliphatic hydrocarbon, the ester of polyhydroxylated aliphatic hydrocarbon or the mixture thereof with the chlorinating agent may be carried out in a reactor as described in application WO 2005/054167 of SOLVAY SA on page 6 lines 3 to 23.

In the process for preparing an organic chlorine product according to the invention, the reaction of the polyhydroxylated aliphatic hydrocarbon, the ester of the polyhydroxylated aliphatic hydrocarbon or the mixture thereof with the chlorinating agent may be carried out in apparatus which is made of or covered with materials that are resistant to chlorinating agents, as described in the patent application entitled "Process for preparing a chlorohydrin in corrosion-resistant apparatus", filed in the name of SOLVAY SA on the same day as the present application, and the content of which is incorporated here by reference.

Particular mention is made of a process for preparing a chlorohydrin that includes a step in which a polyhydroxylated aliphatic hydrocarbon, an ester of a polyhydroxylated aliphatic hydrocarbon or a mixture thereof is subjected to reaction with a chlorinating agent containing hydrogen chloride and to at least one other step carried out in an apparatus made of or covered with materials resistant to the chlorinating agent, under the conditions in which that step is realized. Mention is made more particularly of metallic materials such as enamelled steel, gold and tantalum and of non-metallic materials such as high-density polyethylene, polypropylene, poly(vinylidene fluoride), polytetrafluoroethylene, perfluoroalkoxyalkanes and poly(perfluoropropyl vinyl ether), polysulphones and polysulphides, and unimpregnated and impregnated graphite.

In the process for preparing an organic chlorine product according to the invention, the reaction of the polyhydroxylated aliphatic hydrocarbon, the ester of polyhydroxylated aliphatic hydrocarbon or the mixture thereof with the chlorinating agent may be carried out in a reaction medium as described in the application entitled "Continuous process for preparing chlorohydrins", filed in the name of SOLVAY SA on the same day as the present application, and the content of which is incorporated here by reference.

Particular mention is made of a continuous process for producing chlorohydrin in which a polyhydroxylated aliphatic hydrocarbon, an ester of a polyhydroxylated aliphatic hydrocarbon or a mixture thereof is reacted with a chlorinating agent and an organic acid in a liquid reaction medium whose steady-state composition comprises polyhydroxylated aliphatic hydrocarbon and esters of polyhydroxylated aliphatic hydrocarbon for which the sum of the amounts, expressed in moles of polyhydroxylated aliphatic hydrocarbon, is greater than 1.1 mol % and less than or equal to 30 mol %, the percentage being based on the organic part of the liquid reaction medium.

The organic part of the liquid reaction medium consists of all of the organic compounds of the liquid reaction medium, in other words the compounds whose molecule contains at least one carbon atom.

In the process for preparing an organic chlorine product according to the invention, the reaction of the polyhydroxylated aliphatic hydrocarbon, the ester of polyhydroxylated aliphatic hydrocarbon or the mixture thereof and the chlorinating agent may be carried out in the presence of a catalyst as described in application WO 2005/054167 of SOLVAY SA from page 6 line 28 to page 8 line 5.

Mention is made particularly of a catalyst based on a carboxylic acid or on a carboxylic acid derivative having an atmospheric boiling point of greater than or equal to 200° C., especially adipic acid and derivatives of adipic acid.

In the process for preparing an organic chlorine product according to the invention, the reaction of the polyhydroxylated aliphatic hydrocarbon, the ester of polyhydroxylated aliphatic hydrocarbon or the mixture thereof and the chlorinating agent may be carried out at a catalyst concentration, temperature and pressure and for residence times as described in the application WO 2005/054167 of SOLVAY SA from page 8 line 6 to page 10 line 10.

Mention is made particularly of a temperature of at least 20° C. and not more than 160° C., of a pressure of at least 0.3 bar and not more than 100 bar and of a residence time of at least 1 h and not more than 50 h.

In the process for preparing an organic chlorine product according to the invention, the reaction of the polyhydroxylated aliphatic hydrocarbon, the ester of polyhydroxylated aliphatic hydrocarbon or the mixture thereof with the chlorinating agent may be carried out in the presence of a solvent as described in application WO 2005/054167 of SOLVAY SA at page 11 lines 12 to 36.

Mention is made particularly of organic solvents such as a chlorinated organic solvent, an alcohol, a ketone, an ester or an ether, a non-aqueous solvent which is miscible with the polyhydroxylated aliphatic hydrocarbon, such as chloroethanol, chloropropanol, chloropropanediol, dichloropropanol, dioxane, phenol, cresol and mixtures of chloropropanediol and dichloropropanol, or heavy products of the reaction such as at least partially chlorinated and/or esterified oligomers of the polyhydroxylated aliphatic hydrocarbon.

In the process for preparing an organic chlorine product according to the invention, the reaction of the polyhydroxylated aliphatic hydrocarbon with the chlorinating agent may be carried out in the presence of a liquid phase comprising heavy compounds other than the polyhydroxylated aliphatic hydrocarbon, as described in the application entitled "Process for preparing a chlorohydrin in a liquid phase", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of polyhydroxylated aliphatic hydrocarbon or a mixture thereof is subjected to reaction with a chlorinating agent in the presence of a liquid phase comprising heavy compounds other than the polyhydroxylated aliphatic hydrocarbon and having a boiling temperature under a pressure of 1 bar absolute of at least 15° C. more than the boiling temperature of the chlorohydrin under a pressure of 1 bar absolute.

In the process for preparing an organic chlorine product according to the invention the reaction of the polyhydroxylated aliphatic hydrocarbon, the ester of polyhydroxylated aliphatic hydrocarbon or the mixture thereof with the chlorinating agent is preferably carried out in a liquid reaction medium. The liquid reaction medium may be a single-phase or multi-phase medium.

The liquid reaction medium is composed of all of the dissolved or dispersed solid compounds, dissolved or dispersed liquid compounds and dissolved or dispersed gaseous compounds at the temperature of the reaction.

The reaction medium comprises the reactants, the catalyst, the solvent, the impurities present in the reactants, in the solvent and in the catalyst, the reaction intermediates, the products and the by-products of the reaction.

By reactants are meant the polyhydroxylated aliphatic hydrocarbon, the ester of polyhydroxylated aliphatic hydrocarbon and the chlorinating agent.

Among the impurities present in the polyhydroxylated aliphatic hydrocarbon mention may be made of carboxylic acids, salts of carboxylic acids, esters of fatty acid with the polyhydroxylated aliphatic hydrocarbon, esters of fatty acids with the alcohols used in the transesterification, and inorganic salts such as alkali metal or alkaline earth metal sulphates and chlorides.

When the polyhydroxylated aliphatic hydrocarbon is glycerol, the impurities in the glycerol that may be mentioned include carboxylic acids, salts of carboxylic acids, fatty acid esters such as mono-, di- and triglycerides, esters of fatty acids with the alcohols used in the transesterification and inorganic salts such as alkali metal or alkaline earth metal sulphates and chlorides.

Among the reaction intermediates mention may be made of monochlorohydrins of the polyhydroxylated aliphatic hydrocarbon and their esters and/or polyesters, the esters and/or polyesters of the polyhydroxylated aliphatic hydrocarbon and the esters of polychlorohydrins.

When the chlorohydrin is dichloropropanol, the reaction intermediates that may be mentioned include glycerol monochlorohydrin and its esters and/or polyesters, the esters and/or polyesters of glycerol and the esters of dichloropropanol.

The ester of polyhydroxylated aliphatic hydrocarbon may therefore be, at each instance, a reactant, an impurity of the polyhydroxylated aliphatic hydrocarbon or a reaction intermediate.

By products of the reaction are meant the chlorohydrin and water. The water may be the water formed in the chlorination reaction and/or water introduced into the process, for example via the polyhydroxylated aliphatic hydrocarbon and/or the chlorinating agent, as described in the application WO 2005/054167 of SOLVAY SA at page 2 lines 22 to 28 to page 3 lines 20 to 25, at page 5 lines 7 to 31 and at page 12 lines 14 to 19.

Among the by-products mention may be made for example of the partially chlorinated and/or esterified oligomers of the polyhydroxylated aliphatic hydrocarbon.

When the polyhydroxylated aliphatic hydrocarbon is glycerol, the by-products that may be mentioned include, for example, the partially chlorinated and/or esterified oligomers of glycerol.

The reaction intermediates and the by-products may be formed in the different steps of the process, such as, for example, during the step of preparing the chlorohydrin and during the steps of separating off the chlorohydrin.

The liquid reaction mixture may therefore contain the polyhydroxylated aliphatic hydrocarbon, the chlorinating agent in solution or dispersion in the form of bubbles, the catalyst, the solvent, the impurities present in the reactants, the solvent and the catalyst, such as dissolved or solid salts, for example, the solvent, the catalyst, the reaction intermediates, the products and the by-products of the reaction.

The separation of the chlorohydrin and of the other compounds from the reaction mixture may be carried out in accordance with the methods as described in the application WO 2005/054167 of SOLVAY SA from page 12 line 1 to page 16 line 35 and page 18 lines 6 to 13. These other compounds are those mentioned above and include unconsumed reactants, the impurities present in the reactants, the catalyst, the solvent, the reaction intermediates, the water and the by-products of the reaction.

Particular mention is made of separation by azeotropic distillation of a water/chlorohydrin/chlorinating agent mixture under conditions which minimize the losses of chlorinating agent, followed by isolation of the chlorohydrin by decantation.

In the process for preparing an organic chlorine product according to the invention, the isolation of the chlorohydrin and of the other compounds from the reaction mixture may be carried out in accordance with methods of the kind described in patent application EP 05104321.4, filed in the name of SOLVAY SA on 20 May 2005 and the content of which is incorporated here by reference. Particular mention is made of a separation method including at least one separating operation intended to remove the salt from the liquid phase.

Particular mention is made of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of the polyhydroxylated aliphatic hydrocarbon or a mixture thereof that is used comprises at least one solid or dissolved metal salt, the process including a separation operation intended to remove part of the metal salt. Mention is made more particularly of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of a polyhydroxylated aliphatic hydrocarbon or a mixture thereof that is used comprises at least one sodium and/or potassium chloride and/or sulphate and in which the separating operation intended to remove part of the metal salt is a filtering operation. Particular mention is also made of a process for preparing a chlorohydrin wherein (a) a polyhydroxylated aliphatic hydrocarbon, an ester of a polyhydroxylated aliphatic hydrocarbon or a mixture thereof is subjected to reaction with a chlorinating agent in a reaction mixture, (b) continuously or periodically, a fraction of the reaction mixture containing at least water and the chlorohydrin is removed, (c) at least a part of the fraction obtained in step (b) is introduced into a distillation step and (d) the reflux ratio of the distillation step is controlled by providing water to the said distillation step. Mention is made very particularly of a process for preparing a chlorohydrin wherein (a) a polyhydroxylated aliphatic hydrocarbon, an ester of a polyhydroxylated aliphatic hydrocarbon or a mixture thereof is subjected to reaction with hydrogen chloride in a reaction mixture, (b) continuously or periodically, a fraction of the reaction mixture containing at least water and chlorohydrin is removed, (c) at least part of the fraction obtained in step (b) is introduced into a distillation step in which the ratio between the hydrogen chloride concentration and the water concentration in the fraction introduced into the distillation step is smaller than the hydrogen chloride/water concentration ratio in the binary azeotropic hydrogen chloride/water composition at the distillation temperature and pressure.

In the process for preparing the epoxide according to the invention, the separation of the chlorohydrin and of the other compounds from the reaction mixture from chlorination of the polyhydroxylated aliphatic hydrocarbon, the ester of polyhydroxylated aliphatic hydrocarbon or the mixture thereof may be carried out in accordance with methods as described in the application entitled "Process for preparing a chlorohydrin" filed in the name of SOLVAY SA on the same day as the present application and the content of which is incorporated here by reference.

Particular mention is made of a process for preparing a chlorohydrin which comprises the following steps: (a) a polyhydroxylated aliphatic hydrocarbon, an ester of a polyhydroxylated aliphatic hydrocarbon or a mixture thereof is reacted with a chlorinating agent and an organic acid so as to give a mixture containing the chlorohydrin and esters of the chlorohydrin, (b) at least part of the mixture obtained in (a) is subjected to one or more treatments subsequent to step (a), and (c) the polyhydroxylated aliphatic hydrocarbon is added to at least one of the steps subsequent to step (a), in order to react at a temperature greater than or equal to 20° C. with the esters of the chlorohydrin, so as to form, at least partly, esters of the polyhydroxylated aliphatic hydrocarbon. Mention is made more particularly of a process in which the polyhydroxylated aliphatic hydrocarbon is glycerol and the chlorohydrin is dichloropropanol.

In the process for preparing the epoxide according to the invention, the separation of the chlorohydrin and the other compounds from the reaction mixture from chlorination of the polyhydroxylated aliphatic hydrocarbon, the ester of polyhydroxylated aliphatic hydrocarbon or the mixture thereof may be carried out in accordance with methods as described in the application entitled "Process for preparing a chlorohydrin starting from a polyhydroxylated aliphatic hydrocarbon", filed in the name of SOLVAY SA on the same day as the present application, and the content of which is incorporated here by reference.

Particular mention is made of a process for preparing chlorohydrin by reacting a polyhydroxylated aliphatic hydrocarbon, an ester of a polyhydroxylated aliphatic hydrocarbon or a mixture thereof with a chlorinating agent in a reactor which is supplied with one or more liquid streams containing less than 50% by weight of the polyhydroxylated aliphatic hydrocarbon, of the ester of polyhydroxylated aliphatic hydrocarbon or of the mixture thereof relative to the weight of the entirety of the liquid streams introduced into the reactor. More particular mention is made of a process comprising the following steps: (a) a polyhydroxylated aliphatic hydrocarbon, an ester of a polyhydroxylated aliphatic hydrocarbon or a mixture thereof is reacted with a chlorinating agent so as to give at least one medium containing the chlorohydrin, water and the chlorinating agent, (b) at least a fraction of the medium formed in step (a) is removed, and (c) the fraction removed in step (b) is subjected to an operation of distillation and/or stripping wherein the polyhydroxylated aliphatic hydrocarbon is added in order to isolate, from the fraction removed in step (b), a mixture containing water and the chlorohydrin and exhibiting a reduced chlorinating agent content as compared with the fraction removed in step (b).

In the process for preparing the epoxide according to the invention, the separation of the chlorohydrin and of the other compounds from the reaction mixture from chlorination of the polyhydroxylated aliphatic hydrocarbon may be carried out in accordance with methods as described in the application entitled "Process for converting polyhydroxylated aliphatic hydrocarbons into chlorohydrins", filed in the name of SOLVAY SA on the same day as the present application, and the content of which is incorporated here by reference. Particular mention is made of a process for preparing a chlorohydrin that comprises the following steps: (a) a polyhydroxylated aliphatic hydrocarbon, an ester of a polyhydroxylated aliphatic hydrocarbon or a mixture thereof is reacted with a chlorinating agent so as to give a mixture containing the chlorohydrin, chlorohydrin esters and water, (b) at least a fraction of the mixture obtained in step (a) is subjected to a distillation and/or stripping treatment so as to give a portion concentrated in water, in chlorohydrin and in chlorohydrin esters, and (c) at least a fraction of the portion obtained in step (b) is subjected to a separating operation in the presence of at least one additive so as to obtain a moiety concentrated in chlorohydrin and in chlorohydrin esters and containing less than 40% by weight of water.

The separating operation is more particularly a decantation.

In the process for preparing an organic chlorine product according to the invention, the isolation and the treatment of the other compounds of the reaction mixture may be carried out in accordance with methods as described in the application entitled "Process for preparing a chlorohydrin by chlorinating a polyhydroxylated aliphatic hydrocarbon", filed in the name of SOLVAY SA on the same day as the present application. A preferred treatment consists in subjecting a fraction of the by-products of the reaction to a high-temperature oxidation.

Particular mention is made of a process for preparing a chlorohydrin that comprises the following steps: (a) a polyhydroxylated aliphatic hydrocarbon, an ester of a polyhydroxylated aliphatic hydrocarbon or a mixture thereof whose alkali metal and/or alkaline earth metal content is less than or equal to 5 g/kg, an oxidizing agent and an organic acid are reacted so as to give a mixture containing at least the chlorohydrin and by-products, (b) at least a portion of the mixture obtained in step (a) is subjected to one or more treatments in steps subsequent to step (a), and (c) at least one of the steps subsequent to step (a) consists in an oxidation at a temperature greater than or equal to 800° C. More particular mention is made of a process wherein, in the subsequent step, a portion of the mixture obtained in step (a) is removed and this portion is subjected to oxidation at a temperature greater than or equal to 800° C. in the course of the removal. Particular mention is also made of a process wherein the treatment of step (b) is a separating operation selected from decantation, filtration, centrifugation, extraction, washing, evaporation, stripping, distillation, and adsorption operations or the combinations of at least two of these operations.

In the process according to the invention, when the chlorohydrin is chloropropanol, it is generally employed in the form of a mixture of compounds comprising the isomers of 1-chloropropan-2-ol and 2-chloropropan-1-ol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanol, such as residual reactants, reaction by-products, solvents and, in particular, water.

The mass ratio of the isomers, 1-chloropropan-2-ol and 2-chloropropan-1-ol, is commonly greater than or equal to 0.01, preferably greater than or equal to 0.4. This ratio is commonly less than or equal to 99 and preferably less than or equal to 25.

In the process according to the invention, when the chlorohydrin is chloroethanol, it is generally employed in the form of a mixture of compounds comprising the 2-chloroethanol isomer. This mixture generally contains more than 1% by weight of the isomer, preferably more than 5% by weight and particularly more than 50%. The mixture commonly contains less than 99.9% by weight of the isomer, preferably less than 95% by weight and more particularly less than 90% by weight. The other constituents of the mixture may be compounds originating from the processes for preparing the chloroethanol, such as residual reactants, reaction by-products, solvents and, in particular, water.

In the process according to the invention, when the chlorohydrin is chloropropanediol, it is generally employed in the form of a mixture of compounds comprising the isomers of 1-chloropropane-2,3-diol and 2-chloropropane-1,3-diol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanediol, such as residual reactions, reaction by-products, solvents and, in particular, water.

The mass ratio between the 1-chloropropane-2,3-diol and 2-chloropropane-1,3-diol isomers is commonly greater than or equal to 0.01, preferably greater than or equal to 0.4. This ratio is commonly less than or equal to 99 and preferably less than or equal to 25. In the process according to the invention, when the chlorohydrin is dichloropropanol, it is generally employed in the form of a mixture of compounds comprising the isomers of 1,3-dichloropropan-2-ol and 2,3-dichloropropan-1-ol. This mixture generally contains more than 1% by weight of the two isomers, preferably more than 5% by weight and in particular more than 50%. The mixture commonly contains less than 99.9% by weight of the two isomers, preferably less than 95% by weight and more particularly less than 90% by weight. The other constituents of the mixture may be compounds originating from the processes for preparing the dichloropropanol, such as residual reactants, reaction by-products, solvents and, in particular, water.

The mass ratio between the 1,3-dichloropropan-2-ol and 2,3-dichloropropan-1-ol isomers is commonly greater than or equal to 0.01, often greater than or equal to 0.4, frequently greater than or equal to 1.5, preferably greater than or equal to 3.0, more preferredly greater than or equal to 7.0 and with very particular preference greater than or equal to 20.0. This ratio is commonly less than or equal to 99 and preferably less than or equal to 25.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may take place in the presence of an organic acid. The organic acid may be a product originating from the process for preparing the polyhydroxylated aliphatic hydrocarbon or a product not originating from this process. In this latter case the product in question may be an organic acid which is used in order to catalyse the reaction of the polyhydroxylated aliphatic hydrocarbon with the chlorinating agent. The organic acid may also be an organic acid mixture originating from the process for preparing the polyhydroxylated aliphatic hydrocarbon, and an organic acid not originating from the process for preparing the polyhydroxylated aliphatic hydrocarbon.

In the process according to the invention the esters of the polyhydroxylated aliphatic hydrocarbon may originate from the reaction between the polyhydroxylated aliphatic hydrocarbon and the organic acid, before, during or within the steps which follow the reaction with the chlorinating agent.

The chlorohydrin obtained in the process according to the invention may include a heightened amount of halogenated ketones, in particular of chloroacetone, as described in the patent application FR 05.05120 of 20 May 2005, filed in the name of the applicant, and the content of which is incorporated here by reference. The halogenated ketone content may be reduced by subjecting the chlorohydrin obtained in the process according to the invention to an azeotropic distillation in the presence of water or by subjecting the chlorohydrin to a dehydrochlorination treatment as described in this application from page 4 line 1 to page 6 line 35.

Particular mention is made of a process for preparing an epoxide wherein halogenated ketones are formed as by-products and which comprises at least one treatment of removal of at least a portion of the halogenated ketones formed. Mention is made more particularly of a process for preparing an epoxide by dehydrochlorinating a chlorohydrin of which at least one fraction is prepared by chlorinating a polyhydroxylated aliphatic hydrocarbon, an ester of a polyhydroxylated aliphatic hydrocarbon or a mixture thereof, a treatment of dehydrochlorination and a treatment by azeotropic distillation of a water/halogenated ketone mixture, which are intended to remove at least a portion of the halogenated ketones formed, and a process for preparing epichlorohydrin wherein the halogenated ketone formed is chloroacetone.

The chlorohydrin obtained in the process according to the invention may be subjected to a dehydrochlorination reaction in order to produce an epoxide, as described in the patent applications WO 2005/054167 and FR 05.05120, both filed in the name of SOLVAY SA.

The dehydrochlorination of the chlorohydrin may be carried out as described in the application entitled "Process for preparing an epoxide starting from a polyhydroxylated aliphatic hydrocarbon and a chlorinating agent", filed in the name of SOLVAY SA on the same day as the present application, and the content of which is incorporated here by reference.

Particular mention is made of a process for preparing an epoxide wherein a reaction mixture resulting from the reaction between a polyhydroxylated aliphatic hydrocarbon, an ester of a polyhydroxylated aliphatic hydrocarbon or a mixture thereof with a chlorinating agent, the reaction mixture containing at least 10 g of chlorohydrin per kg of reaction mixture, is subjected to a subsequent chemical reaction without intermediate treatment.

Mention is also made of the preparation of an epoxide that comprises the following steps: (a) a polyhydroxylated aliphatic hydrocarbon, an ester of a polyhydroxylated aliphatic hydrocarbon or a mixture thereof is reacted with a chlorinating agent and an organic acid so as to form the chlorohydrin and chlorohydrin esters in a reaction mixture containing the polyhydroxylated aliphatic hydrocarbon, the ester of polyhydroxylated aliphatic hydrocarbon, water, the chlorinating agent and the organic acid, the reaction mixture containing at least 10 g of chlorohydrin per kg of reaction mixture, (b) at least a fraction of the reaction mixture obtained in step (a), this fraction having the same composition as the reaction mixture obtained in step (a), is subjected to one or more treatments in steps subsequent to step (a), and (c) a basic compound is added to at least one of the steps subsequent to step (a) in order to react at least partly with the chlorohydrin, the chlorohydrin esters, the chlorinating agent and the organic acid so as to form the epoxide and salts.

In the process for preparing an organic chlorine product according to the invention, the process for preparing the chlorohydrin may be integrated within an overall plan for preparation of an epoxide, as described in the application entitled "Process for preparing an epoxide starting from a chlorohydrin", filed in the name of SOLVAY SA on the same day as the present application, and the content of which is incorporated here by reference.

Particular mention is made of a process for preparing an epoxide that comprises at least one step of purification of the epoxide formed, the epoxide being at least partly prepared by a process of dehydrochlorinating a chlorohydrin, the latter being at least partly prepared by a process of chlorinating a polyhydroxylated aliphatic hydrocarbon, an ester of a polyhydroxylated aliphatic hydrocarbon or a mixture thereof.

The various processes forming part of the process for preparing a chlorohydrin according to the invention may or may not form part of an integrated process for preparing organic chlorine products. An integrated process is preferred.

The invention likewise provides plant for implementing an integrated process, comprising:
(a) a unit for preparing allyl chloride and/or a unit for preparing chloromethanes and/or a chlorinolysis unit and/or a unit for oxidizing chlorine compounds, from which exits a chlorinating agent comprising hydrogen chloride,
(b) a unit for preparing a chlorohydrin by chlorination of a polyhydroxylated hydrocarbon, of an ester of a polyhydroxylated aliphatic hydrocarbon or of a mixture thereof, the said unit being supplied with the chlorinating agent from unit (a) and from which exits the chlorohydrin,
(c) a unit for preparing an epoxide by dehydrochlorination of the chlorohydrin, the said unit being supplied with chlorohydrin from unit (b) and from which exits the epoxide.

This plant may comprise:
(d) a unit for preparing epoxy resins which is supplied with the epoxide from unit (c).

The different preparation units are preferably distributed over a single industrial site or over nearby sites, more preferably over a single site. The industrial plan embracing these units on a single site or on nearby sites is particularly advantageous: for example, a unit according to the aforementioned process for preparing chlorohydrin in proximity to units for preparing allyl chloride and epoxides, with the optional addition of a chlorinolysis unit and/or a unit for preparing chloromethane and/or a unit for high-temperature oxidation of chlorine compounds. By nearby sites are meant, in particular, industrial sites which are sufficiently close that the transport of materials between the plants can be accomplished economically via pipelines.

In the process and plant according to the invention, the polyhydroxylated aliphatic hydrocarbon is preferably glycerol, the chlorohydrin is preferably dichloropropanol and the epoxide is preferably epichlorohydrin.

When the epoxide is epichlorohydrin it may be employed in the preparation of epoxy resins.

FIG. 1 shows a particular plan of plant which can be used to implement the process according to the invention when the polyhydroxylated aliphatic hydrocarbon is glycerol, the chlorohydrin is dichloropropanol and the epoxide is epichlorohydrin.

A dichloropropanol dehydrochlorination unit (1) is supplied with dichloropropanol via line (2) and with dehydrochlorinating agent via line (3). Epichlorohydrin is withdrawn via line (4) and organic compounds other than epichlorohydrin via line (5). At least a fraction of these compounds may supply a chlorinolysis plant (21) via line (33) and/or a plant for high-temperature oxidation of chlorine compounds (23) via line (34). The epichlorohydrin supplies a unit for preparing epoxy resins (8) via line (6) and/or a unit for preparing polyglycerols (9) via line (7). The dichloropropanol originates from a unit for hypochlorinating allyl chloride (10) via line (11) and/or from a unit for chlorinating glycerol (12) via line (13). The unit for chlorinating glycerol (12) is supplied with crude and/or purified glycerol via line (14). The crude and/or purified glycerol originates from a unit for producing biodiesel (15), from which biodiesel is likewise withdrawn, via line (37), and which is supplied with animal and/or vegetable oils and/or fats via line (16) and with alcohol, preferably methanol, via line (17). The unit for chlorinating glycerol (12) is supplied with hydrogen chloride and/or with aqueous hydrogen chloride solution via line (18). The hydrogen chloride and/or the aqueous solution of hydrogen chloride originate from a unit for preparing allyl chloride by chlorinating propylene (19) via line (20) and/or from a unit for preparing chloromethanes (35) via line (36) and/or from a chlorinolysis unit (21) via line (22) and/or from a high-temperature oxidation unit (23) via line (24). Allyl chloride is withdrawn from unit (19) and at least a fraction of this allyl chloride is supplied to the hypochlorination unit (10) via line (25). Organic compounds other than allyl chloride are withdrawn from the unit for preparing allyl chloride (19) via line (26), and at least a fraction thereof is used to supply the chlorinolysis unit (21) via line (27) and/or the unit for high-temperature oxidation of chlorine compounds (23) via line (28). Perchloroethylene and carbon tetrachloride are withdrawn via line (29) from the chlorinolysis unit (21), and organic compounds other than perchloroethylene and carbon tetrachloride are withdrawn therefrom via line (30), and at least a fraction of these compounds may be recycled to the chlorinolysis unit via line (31) and/or may supply the unit for high-temperature oxidation of chlorine compounds (23) via line (32). The chlorinolysis unit and the unit for high-temperature oxidation of chlorine compounds may be supplied with organic products obtained from preparation units other than those mentioned. The unit for preparing dichloropropanol may be supplied with hydrogen chloride and/or hydrochloric acid obtained from preparation processes other than those mentioned above.

The advantages derived from this plan include the following:
(a) an advantageous utilization of the acids and organic products co-produced in the various preparation processes;
(b) a limitation of transportation of dangerous materials, with elimination of the costs associated with such transportation;
(c) a sharing of plant between the two epichlorohydrin synthesis processes, such as the dehydrochlorination step, for example;
(d) the re-use of waters obtained from the processes, contaminated by organic substances, or the invert waters from these plants, either to the unit for hypochlorinating allyl chloride to dichloropropanol (19) or to the dehydrochlorination unit (1). The waters obtained from the processes are, for example, the waters obtained from pumps or ejectors which serve to maintain the vacuum in the plants. They may also be the waters obtained after decantation from the organic substances.

The invention claimed is:

1. A process for preparing dichloropropanol comprising reacting glycerol, an ester of glycerol or a mixture thereof with hydrogen chloride wherein the hydrogen chloride is (I) gaseous hydrogen chloride comprising not more than 15% by volume of water and not more than 5% by volume of nitrogen, or (III) a combination thereof of gaseous hydrogen chloride comprising not more than 15% by volume of water and not more than 5% by volume of nitrogen and an aqueous solution of hydrogen chloride, and wherein the hydrogen chloride comprises at least one of the following substances in a positive amount not exceeding the maxima indicated below, where the amount calculated in the gaseous hydrogen chloride does not take into account the water and nitrogen and in the aqueous solution of hydrogen chloride does not take into account the water:
oxygen: 5% by volume
hydrogen: 0.1% by volume
chlorine: 2000 ppm by volume
methane: 10 000 ppm by volume
carbon monoxide: 10 000 ppm by volume
carbon dioxide: 10 000 ppm by volume
organic hydrocarbon products: 50 000 ppm by volume
organic chlorine products: 50 000 ppm by volume
organic fluorine products: 50 000 ppm by volume
organic oxygen products: 50 000 ppm by volume
propylene: 10 000 ppm by volume
monochloropropenes: 15 000 ppm by volume
chloropropane: 10 000 ppm by volume,
organic oxygen compounds: 5000 ppm by volume, and
in addition to the above, when the hydrogen chloride includes an aqueous solution of hydrogen chloride:
metals, taken individually: 5 ppm by weight.

2. The process according to claim 1, wherein the hydrogen chloride comprises organic hydrocarbon products selected from saturated and unsaturated aliphatic and aromatic hydrocarbons and mixtures thereof.

3. The process according to claim 2, wherein the unsaturated aliphatic hydrocarbon is selected from the group consisting of acetylene, ethylene, propylene, butene, propadiene and methylacetylene, the saturated aliphatic hydrocarbon is selected from the group consisting of methane, ethane, propane and butane and the aromatic hydrocarbon is benzene.

4. The process according to claim 1, wherein the hydrogen chloride comprises an organic chlorine product selected from the group consisting of chloromethanes, chloroethanes, chloropropanes, chlorobutanes, vinyl chloride, vinylidene chloride, monochloropropenes, perchloroethylene, trichloroethylene, chlorobutadienes, chlorobenzenes and mixtures thereof.

5. The process according to claim 1, wherein the hydrogen chloride comprises an organic fluorine product selected from the group consisting of fluoromethanes, fluoroethanes, vinyl fluoride, vinylidene fluoride and mixtures thereof.

6. The process according to claim 1, wherein the hydrogen chloride comprises an organic oxygen compound selected from the group consisting of alcohols, chloroalcohols, chloroethers and mixtures thereof.

7. The process according to claim 1, wherein the hydrogen chloride is obtained at least partly from a process for preparing allyl chloride and/or a process for preparing chloromethanes and/or a process of chlorinolysis and/or a process for oxidizing chlorine compounds at a temperature greater than or equal to 800° C.

8. The process according to claim 1, wherein the hydrogen chloride is a combination of said gaseous hydrogen chloride and said aqueous solution of hydrogen chloride.

9. The process according to claim 1, further comprising preparing epichlorohydrin by dehydrochlorinating said dichloropropanol.

10. The process according to claim 9, further comprising preparing an epoxy resin from said epichlorohydrin.

11. The process according to claim 1, wherein the hydrogen chloride is said gaseous hydrogen chloride comprising not more than 15% by volume of water and not more than 5% by volume of nitrogen.

12. A process for preparing a chlorohydrin comprising reacting polyhydroxylated aliphatic hydrocarbon, an ester of a polyhydroxylated aliphatic hydrocarbon or a mixture thereof with a chlorinating agent, the chlorinating agent comprising at least one of the following: fluoromethanes, fluoroethanes, vinyl fluoride, vinylidene fluoride, alcohols, chloroalcohols, chloroethers, and mixtures thereof.

13. The process according to claim 12, wherein the polyhydroxylated aliphatic hydrocarbon is selected from the group consisting of ethylene glycol, propylene glycol, chloropropanediol, glycerol and mixtures of at least two thereof.

14. The process according to claim 12, wherein the chlorohydrin is selected from the group consisting of chloroethanol, chloropropanol, chloropropanediol, dichloropropanol and mixtures of at least two thereof.

15. The process according to claim 12, wherein the polyhydroxylated aliphatic hydrocarbon is glycerol, and the chlorohydrin is dichloropropanol.

16. The process according to claim 12, wherein the chlorinating agent comprises at least one of the following: fluoromethanes, fluoroethanes, vinyl fluoride, vinylidene fluoride and mixtures thereof.

17. The process according to claim 12, wherein the chlorinating agent comprises at least one of the following: alcohols, chloroalcohols, chloroethers and mixtures thereof.

18. A process for preparing a chlorohydrin comprising reacting polyhydroxylated aliphatic hydrocarbon, an ester of a polyhydroxylated aliphatic hydrocarbon or a mixture thereof with a chlorinating agent, the chlorinating agent comprising at least one of the following: alkali metals, alkaline earth metals, iron, nickel, copper, lead, arsenic, cobalt, titanium, cadmium, antimony, mercury, zinc, selenium, aluminium, bismuth and mixtures thereof.

19. The process according to claim 12, wherein said chlorohydrin is dichloropropanol, said method further comprising preparing epichlorohydrin by dehydrochlorinating said dichloropropanol.

20. The process according to claim 19, further comprising preparing an epoxy resin from said epichlorohydrin.

21. The process according to claim 18, wherein said chlorohydrin is dichloropropanol, said method further comprising preparing epichlorohydrin by dehydrochlorinating said dichloropropanol.

22. The process according to claim 21, further comprising preparing an epoxy resin from said epichlorohydrin.

23. A process for preparing dichloropropanol comprising reacting glycerol, an ester of glycerol or a mixture thereof with hydrogen chloride wherein the hydrogen chloride is (I) gaseous hydrogen chloride comprising not more than 15% by volume of water and not more than 5% by volume of nitrogen, (II) an aqueous solution of hydrogen chloride, or (III) a combination thereof, and wherein the hydrogen chloride comprises at least one of the following substances in a positive amount not exceeding the maxima indicated below, where the amount calculated in the gaseous hydrogen chloride does not take into account the water and nitrogen and in the aqueous solution of hydrogen chloride does not take into account the water:

organic fluorine products: 50 000 ppm by volume, and organic oxygen products: 50 000 ppm by volume wherein the organic fluorine products are selected from the group consisting of fluoromethanes, fluoroethanes, vinyl fluoride, vinylidene fluoride and mixtures thereof, and the organic oxygen compounds are selected from the group consisting of alcohols, chloroalcohols, chloroethers and mixtures thereof.

24. The process according to claim 23, wherein the hydrogen chloride comprises an organic fluorine product selected from the group consisting of fluoromethanes, fluoroethanes, vinyl fluoride, vinylidene fluoride and mixtures thereof.

25. The process according to claim 23, wherein the hydrogen chloride comprises an organic oxygen compound selected from the group consisting of alcohols, chloroalcohols, chloroethers and mixtures thereof.

* * * * *

UNITED STATES PATENT AND TRADEMARK OFFICE
CERTIFICATE OF CORRECTION

PATENT NO. : 8,344,185 B2
APPLICATION NO. : 11/914868
DATED : January 1, 2013
INVENTOR(S) : Philippe Krafft It is certified that error appears in the above-identified patent and that said Letters Patent is hereby corrected as shown below:

Column 22, Line 23 "or (III) a combination thereof of gaseous hydrogen chloride" should read -- a combination of gaseous hydrogen chloride --

Signed and Sealed this
Twenty-sixth Day of March, 2013

Teresa Stanek Rea
*Acting Director of the United States Patent and Trademark Office*